US00RE46626E

(19) United States
(12) Reissued Patent
Karlsson et al.

(10) Patent Number: US RE46,626 E
(45) Date of Reissued Patent: Dec. 12, 2017

(54) DENTAL IMPRESSION TRAY FOR USE IN OBTAINING AN IMPRESSION OF A DENTAL STRUCTURE

(71) Applicant: Nobel Biocare Services AG, Kloten (CH)

(72) Inventors: Per-Olof Karlsson, Alingsas (SE); Jenny Fäldt, Mölnlycke (SE)

(73) Assignee: Nobel Biocare Services AG, Kloten (CH)

(21) Appl. No.: 14/963,159

(22) Filed: Dec. 8, 2015

Related U.S. Patent Documents

Reissue of:
(64) Patent No.: 8,602,773
Issued: Dec. 10, 2013
Appl. No.: 12/447,461
PCT Filed: Oct. 18, 2007
PCT No.: PCT/SE2007/000925
§ 371 (c)(1),
(2) Date: Jun. 24, 2009
PCT Pub. No.: WO2008/051142
PCT Pub. Date: May 2, 2008

(30) Foreign Application Priority Data

Oct. 27, 2006 (SE) ..... 0602272

(51) Int. Cl.
*A61C 9/00* (2006.01)

(52) U.S. Cl.
CPC ..... *A61C 9/0006* (2013.01); *A61C 9/0093* (2013.01)

(58) Field of Classification Search
CPC ..... A61C 9/0006
USPC ..... 433/37–49, 72, 73, 53–68, 80, 82–87, 433/118, 119, 215, 216, 6, 77, 79, 126
See application file for complete search history.

(56) References Cited

U.S. PATENT DOCUMENTS 1,798,518 A 3/1931 Bennett
2,445,639 A 7/1948 Sandhofer
4,252,523 A 2/1981 Gayso
4,552,531 A * 11/1985 Martin ..... 433/147
(Continued)

FOREIGN PATENT DOCUMENTS

DE 602015 8/1934
DE 10061088 6/2002
(Continued)

OTHER PUBLICATIONS

International Search Report received in corresponding PCT Application No. PCT/SE2007/000925, dated Feb. 6, 2008, 4 pages.
(Continued)

*Primary Examiner* — Cary Wehner
(74) *Attorney, Agent, or Firm* — Knobbe, Martens, Olson & Bear LLP

(57) ABSTRACT

A dental impression tray, a kit, and method of using the same are provided for taking an impression of at least a portion of a dental structure of a patient. The tray can include a tray portion, fiduciary markers, and can also have a holding section with two opposing sides and fasteners disposed thereon. The kit can include the tray and a handle portion. The handle can be removably secured to the holding section of the tray. In some embodiments, the handle can include a pair of handle portions. In other embodiments, a part of the handle can be aligned with a facial feature of a patient from whom a dental impression is to be obtained.

7 Claims, 19 Drawing Sheets

(56) References Cited

U.S. PATENT DOCUMENTS 4,854,868 A 8/1989 Pitre
5,052,928 A 10/1991 Andersson
5,059,758 A 10/1991 Andersson
5,069,622 A 12/1991 Rangert et al.
5,076,785 A 12/1991 Tsai
5,192,173 A 3/1993 Andersson et al.
5,192,472 A 3/1993 Andersson
5,338,198 A 8/1994 Wu et al.
5,382,164 A 1/1995 Stern
5,440,496 A 8/1995 Andersson et al.
5,497,336 A 3/1996 Andersson et al.
5,549,476 A 8/1996 Stern
5,565,152 A 10/1996 Odén et al.
5,587,912 A 12/1996 Andersson et al.
5,607,305 A 3/1997 Andersson et al.
5,652,709 A 7/1997 Andersson et al.
5,674,073 A 10/1997 Ingber et al.
5,690,490 A 11/1997 Cannon et al.
5,725,376 A 3/1998 Poirier
5,733,126 A 3/1998 Andersson et al.
5,752,826 A 5/1998 Andreiko
5,752,828 A 5/1998 Andersson et al.
5,800,174 A 9/1998 Andersson
5,851,115 A 12/1998 Carlsson et al.
5,857,853 A 1/1999 van Nifterick et al.
5,880,962 A 3/1999 Andersson et al.
5,938,446 A 8/1999 Andersson et al.
5,975,893 A 11/1999 Chishti et al.
6,062,791 A * 5/2000 Simon ..... 411/535
6,062,861 A 5/2000 Andersson
6,099,314 A 8/2000 Kopelman et al.
6,152,731 A 11/2000 Jordan et al.
6,206,693 B1 3/2001 Hultgren
6,212,442 B1 4/2001 Andersson et al.
6,217,325 B1 4/2001 Chishti et al.
6,217,334 B1 4/2001 Hultgren
6,227,850 B1 5/2001 Chishti et al.
6,261,098 B1 7/2001 Persson
6,283,752 B1 9/2001 Kumar
6,287,119 B1 9/2001 van Nifterick et al.
6,302,690 B1 * 10/2001 Brandhorst et al. ..... 433/45
6,318,994 B1 11/2001 Chishti et al.
6,322,359 B1 11/2001 Jordan et al.
6,341,694 B1 1/2002 Dawood
6,371,761 B1 4/2002 Cheang et al.
6,382,975 B1 5/2002 Poirier
6,382,977 B1 5/2002 Kumar
6,386,878 B1 5/2002 Pavlovskaia et al.
6,398,548 B1 6/2002 Muhammad et al.
6,406,292 B1 6/2002 Chishti et al.
6,413,085 B1 * 7/2002 Lee ..... 433/56
6,431,871 B1 8/2002 Luthardt
6,450,807 B1 9/2002 Chishti et al.
6,457,972 B1 10/2002 Chishti et al.
6,463,344 B1 10/2002 Pavloskaia et al.
6,471,511 B1 10/2002 Chishti et al.
6,497,574 B1 12/2002 Miller
6,511,318 B2 1/2003 Kim
6,554,611 B2 4/2003 Chishti et al.
6,558,162 B1 5/2003 Porter et al.
6,561,805 B2 5/2003 Kumar
6,579,095 B2 6/2003 Marshall et al.
6,582,229 B1 6/2003 Miller et al.
6,602,070 B2 8/2003 Miller et al.
6,607,386 B1 8/2003 Andersson et al.
6,626,666 B2 9/2003 Chishti et al.
6,629,840 B2 10/2003 Chishti et al.
6,633,789 B1 10/2003 Nikolskiy et al.
6,640,150 B1 10/2003 Persson et al.
6,655,962 B1 12/2003 Kennard
6,665,570 B2 12/2003 Pavloskaia et al.
6,671,539 B2 12/2003 Gateno et al.
6,682,346 B2 1/2004 Chishti et al.
6,685,469 B2 2/2004 Chishti et al.
6,688,886 B2 2/2004 Hughes et al.
6,697,164 B1 2/2004 Babayoff et al.
6,699,037 B2 3/2004 Chishti et al.
6,705,863 B2 3/2004 Phan et al.
6,722,880 B2 4/2004 Chishti et al.
6,726,478 B1 4/2004 Isiderio et al.
6,729,876 B2 5/2004 Chishti et al.
6,767,208 B2 7/2004 Kaza
6,769,913 B2 8/2004 Hurson
6,783,360 B2 8/2004 Chishti
6,786,721 B2 9/2004 Chishti et al.
6,790,040 B2 9/2004 Amber et al.
6,802,713 B1 10/2004 Chishti et al.
6,814,575 B2 11/2004 Poirier
6,821,123 B2 11/2004 Andersson et al.
6,940,611 B2 9/2005 Babayoff et al.
6,948,936 B2 9/2005 Miller et al.
6,964,568 B1 * 11/2005 Segal ..... 433/45
6,979,196 B2 12/2005 Nikolskiy et al.
7,030,383 B2 4/2006 Babayoff et al.
7,037,111 B2 5/2006 Miller
7,040,896 B2 5/2006 Pavlovskaia et al.
7,059,850 B1 6/2006 Phan et al.
7,074,038 B1 7/2006 Miller
7,089,070 B1 8/2006 Andersson et al.
7,092,107 B2 8/2006 Babayoff et al.
7,092,780 B2 8/2006 Ganley et al.
7,092,784 B1 8/2006 Simkins
7,101,178 B2 9/2006 Diesso
7,118,375 B2 10/2006 Durbin et al.
7,134,874 B2 11/2006 Chishti et al.
7,140,877 B2 11/2006 Kaza
7,142,312 B2 11/2006 Quadling et al.
7,156,661 B2 1/2007 Choi et al.
7,175,435 B2 2/2007 Andersson et al.
7,202,466 B2 4/2007 Babayoff et al.
7,214,946 B2 5/2007 Babayoff et al.
7,220,122 B2 5/2007 Chishti
7,220,124 B2 5/2007 Taub et al.
7,230,725 B2 6/2007 Babayoff et al.
7,241,142 B2 7/2007 Abolfathi et al.
7,252,507 B2 8/2007 Tesini
7,255,558 B2 8/2007 Babayoff et al.
7,273,367 B2 9/2007 Hughes et al.
7,286,954 B2 10/2007 Kopelman et al.
7,319,529 B2 1/2008 Babayoff
7,320,592 B2 1/2008 Chishti et al.
7,326,051 B2 2/2008 Miller
7,331,783 B2 2/2008 Chishti et al.
7,331,786 B2 2/2008 Poirier
7,333,874 B2 2/2008 Taub et al.
7,347,690 B2 3/2008 Jordan et al.
7,357,634 B2 4/2008 Knopp
7,361,020 B2 4/2008 Abolfathi et al.
7,362,890 B2 4/2008 Scharlack et al.
7,363,239 B1 4/2008 Andersson et al.
7,373,286 B2 5/2008 Nikolskiy et al.
7,377,778 B2 5/2008 Chishti et al.
7,425,131 B2 9/2008 Amber et al.
7,428,481 B2 9/2008 Nikolskiy et al.
7,433,810 B2 10/2008 Pavloskaia et al.
7,435,083 B2 10/2008 Chishti et al.
7,442,040 B2 10/2008 Kuo
7,452,207 B2 11/2008 Miller et al.
7,472,789 B2 1/2009 Wu et al.
7,473,097 B2 * 1/2009 Raby et al. ..... 433/24
7,474,307 B2 1/2009 Chishti et al.
7,476,100 B2 1/2009 Kuo
7,477,402 B2 1/2009 Babayoff et al.
7,511,829 B2 3/2009 Babayoff
7,536,234 B2 5/2009 Kopelman et al.
7,547,873 B2 6/2009 Babayoff et al.
7,555,403 B2 6/2009 Kopelman et al.
7,601,000 B1 * 10/2009 Hammond et al. ..... 433/68
7,835,811 B2 * 11/2010 Schmitt ..... 700/98
2001/0002310 A1 5/2001 Chishti et al.
2001/0006770 A1 7/2001 Chishti et al.
2001/0008751 A1 7/2001 Chishti et al.
2001/0009753 A1 7/2001 Chishti et al.
2002/0064747 A1 5/2002 Chishti et al.

(56) References Cited

U.S. PATENT DOCUMENTS

2002/0064748 A1 5/2002 Chishti et al.
2002/0064759 A1 5/2002 Durbin et al.
2002/0094509 A1 7/2002 Durbin et al.
2002/0119423 A1 8/2002 Chishti et al.
2002/0150855 A1 10/2002 Shishti et al.
2002/0177108 A1 11/2002 Pavlovskaia et al.
2003/0003416 A1 1/2003 Chishti et al.
2003/0008259 A1 1/2003 Kuo et al.
2003/0009252 A1 1/2003 Pavlovskaia et al.
2003/0064345 A1 4/2003 Chishti et al.
2003/0138754 A1* 7/2003 DiMarino et al. ..... 433/37
2003/0139834 A1 7/2003 Nikolskiy et al.
2003/0160784 A1 8/2003 Kopelman et al.
2003/0198917 A1 10/2003 Miller et al.
2003/0207227 A1 11/2003 Abolfathi
2003/0232302 A1 12/2003 Babayoff et al.
2003/0235803 A1 12/2003 Nikolskiy et al.
2004/0023183 A1 2/2004 Miller et al.
2004/0023188 A1 2/2004 Pavlovskaia et al.
2004/0090638 A1 5/2004 Babayoff et al.
2004/0096799 A1 5/2004 Hughes et al.
2004/0110110 A1 6/2004 Chishti et al.
2004/0128010 A1 7/2004 Pavlovskaia et al.
2004/0137400 A1 7/2004 Chishti et al.
2004/0137406 A1 7/2004 Kennard
2004/0166456 A1 8/2004 Chishti et al.
2004/0170943 A1 9/2004 Chishti et al.
2004/0172150 A1 9/2004 Perot et al.
2004/0175671 A1 9/2004 Jones et al.
2004/0191719 A1 9/2004 Kaza
2004/0204787 A1 10/2004 Kopelman et al.
2004/0219490 A1 11/2004 Gartner et al.
2004/0224286 A1 11/2004 Kaza et al.
2004/0243361 A1 12/2004 Steuben et al.
2004/0259051 A1 12/2004 Brajnovic
2005/0019721 A1 1/2005 Chishti
2005/0026102 A1 2/2005 Miller
2005/0048432 A1 3/2005 Choi et al.
2005/0055118 A1 3/2005 Nikolskiy et al.
2005/0079468 A1 4/2005 Chishti et al.
2005/0105974 A1* 5/2005 Ben-Mucha ..... 407/103
2005/0106528 A1 5/2005 Abolfathi et al.
2005/0106529 A1 5/2005 Abolfathi et al.
2005/0186524 A1 8/2005 Abolfathi et al.
2005/0191593 A1 9/2005 Knopp
2005/0192835 A1 9/2005 Kuo et al.
2005/0196724 A1 9/2005 Miller et al.
2005/0208449 A1 9/2005 Abolfathi et al.
2005/0244768 A1 11/2005 Taub et al.
2005/0244782 A1 11/2005 Chishti et al.
2005/0264828 A1 12/2005 Babayoff et al.
2005/0277091 A1 12/2005 Andersson et al.
2006/0003292 A1 1/2006 Lauren et al.
2006/0008777 A1 1/2006 Peterson et al.
2006/0040236 A1 2/2006 Schmitt
2006/0068355 A1 3/2006 Schultz
2006/0093987 A1 5/2006 Wen
2006/0093993 A1 5/2006 Wen
2006/0095242 A1 5/2006 Marshall
2006/0097178 A1 5/2006 Babayoff et al.
2006/0106484 A1 5/2006 Saliger et al.
2006/0127859 A1 6/2006 Wen
2006/0158665 A1 7/2006 Babayoff et al.
2006/0212260 A1 9/2006 Kopelman et al.
2006/0263738 A1 11/2006 Kuo
2006/0286501 A1 12/2006 Chishti et al.
2007/0003907 A1 1/2007 Chishti et al.
2007/0026363 A1 2/2007 Lehmann et al.
2007/0031774 A1 2/2007 Cinader, Jr. et al.
2007/0077537 A1 4/2007 Taub et al.
2007/0087302 A1 4/2007 Reising et al.
2007/0092850 A1 4/2007 Kaza
2007/0092854 A1 4/2007 Powell et al.
2007/0109559 A1 5/2007 Babayoff et al.
2007/0128573 A1 6/2007 Kuo
2007/0128574 A1 6/2007 Kuo et al.
2007/0129991 A1 6/2007 Kuo
2007/0134613 A1 6/2007 Kuo et al.
2007/0134617 A1 6/2007 Babayoff et al.
2007/0141525 A1 6/2007 Cinader, Jr.
2007/0141527 A1 6/2007 Kuo et al.
2007/0145248 A1 6/2007 Babayoff et al.
2007/0154867 A1 7/2007 Taub et al.
2007/0164203 A1 7/2007 Babayoff et al.
2007/0168152 A1 7/2007 Matov et al.
2007/0190481 A1 8/2007 Schmitt
2007/0190492 A1 8/2007 Schmitt
2007/0203663 A1 8/2007 Kopelman et al.
2007/0238065 A1 10/2007 Sherwood et al.
2007/0243503 A1 10/2007 Gagnon et al.
2007/0281284 A1 12/2007 Andersson et al.
2007/0292004 A1 12/2007 Peters
2007/0293748 A1 12/2007 Engvall et al.
2008/0002869 A1 1/2008 Scharlack et al.
2008/0015727 A1 1/2008 Dunne et al.
2008/0024768 A1 1/2008 Babayoff
2008/0038684 A1 2/2008 Keating et al.
2008/0038688 A1 2/2008 Kopelman et al.
2008/0038692 A1 2/2008 Andersson et al.
2008/0044786 A1 2/2008 Kalili
2008/0057466 A1 3/2008 Jordan et al.
2008/0070181 A1 3/2008 Abolfathi et al.
2008/0085487 A1 4/2008 Kuo et al.
2008/0090211 A1 4/2008 Andersson
2008/0124681 A1 5/2008 Cha
2008/0131832 A1 6/2008 Miller
2008/0131841 A1 6/2008 Taub et al.
2008/0160473 A1 7/2008 Li et al.
2008/0166676 A1 7/2008 Chishti et al.
2008/0182220 A1 7/2008 Chishti et al.
2008/0182221 A1 7/2008 Chishti et al.
2008/0187879 A1 8/2008 Chishti et al.
2008/0193899 A1 8/2008 Karlsson et al.
2008/0206705 A1 8/2008 Kaza et al.
2008/0206710 A1 8/2008 Kruth et al.
2008/0206714 A1 8/2008 Schmitt
2008/0248443 A1 10/2008 Chishti et al.
2008/0259411 A1 10/2008 Karlsson
2008/0261176 A1 10/2008 Hurson
2008/0268400 A1 10/2008 Moss et al.
2008/0286716 A1 11/2008 Sherwood
2008/0286717 A1 11/2008 Sherwood
2008/0288289 A1 11/2008 Sah
2008/0300716 A1 12/2008 Kopelman et al.
2008/0305452 A1 12/2008 Sterental et al.
2008/0305453 A1 12/2008 Kitching et al.
2008/0306724 A1 12/2008 Kitching et al.
2008/0316209 A1 12/2008 Wen
2009/0148807 A1 6/2009 Babayoff et al.
2009/0148809 A1 6/2009 Kuo et al.
2009/0153858 A1 6/2009 Babayoff
2009/0153879 A1 6/2009 Babayoff et al.

FOREIGN PATENT DOCUMENTS

EP 1957005 8/2008
FR 1438237 4/1966
SE 441333 9/1985
SE 531381 C2 3/2009
WO WO 2005/046504 5/2005
WO WO 2007/062658 6/2007
WO WO 2008/051130 5/2008
WO WO 2008/051141 5/2008

OTHER PUBLICATIONS

Written Opinion of the International Searching Authority for International application No. PCT/SE2007/000925, dated Feb. 6, 2008, in 6 pages.

(56) References Cited

OTHER PUBLICATIONS

International Preliminary Report on Patentability for International application No. PCT/SE2007/000925, dated Apr. 28, 2009, in 7 pages.

* cited by examiner

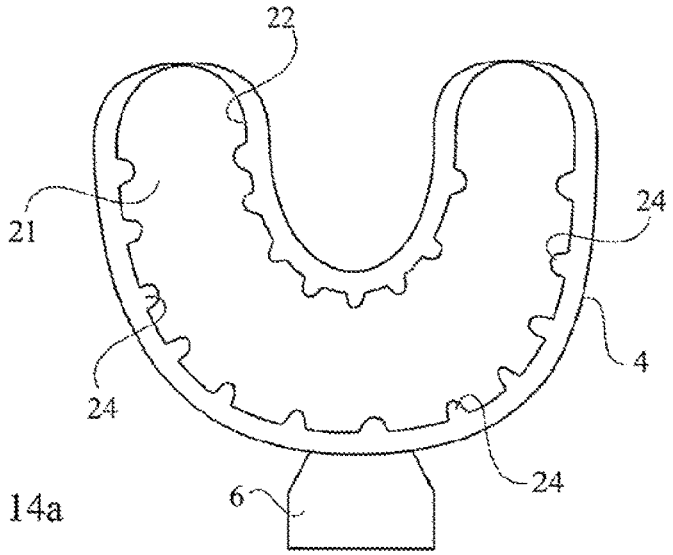
Fig. 14a
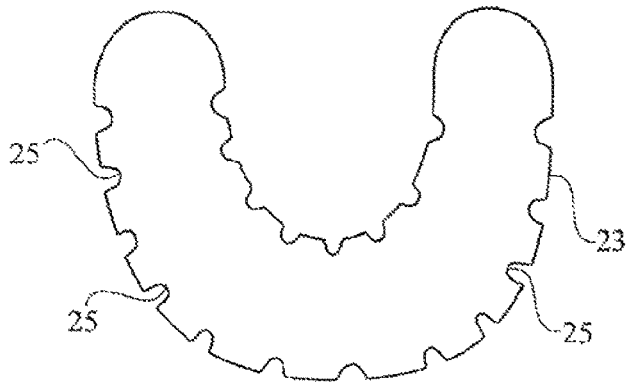
Fig. 14b
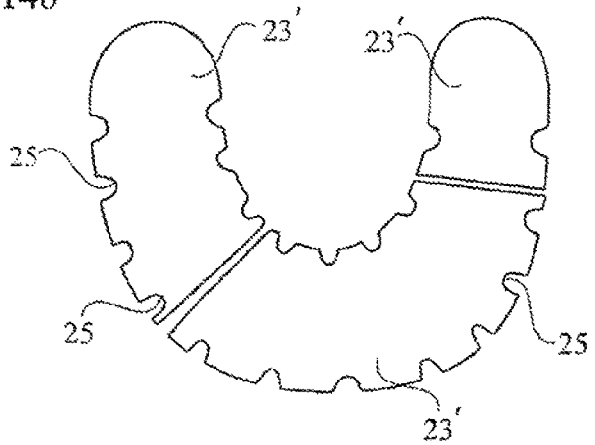

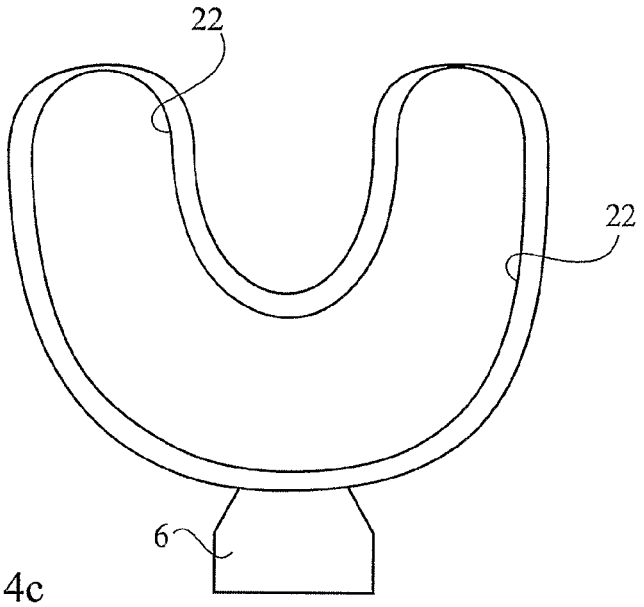
Fig. 14c
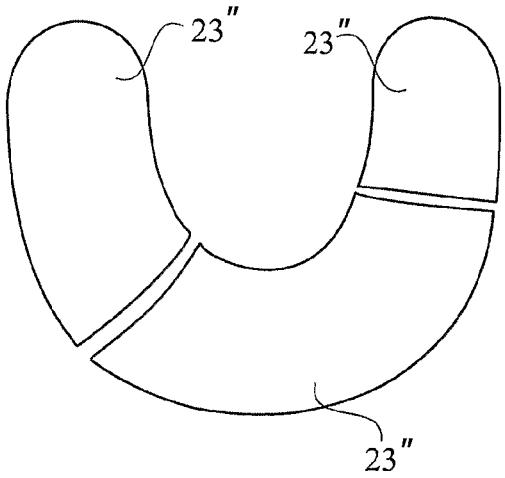

DENTAL IMPRESSION TRAY FOR USE IN OBTAINING AN IMPRESSION OF A DENTAL STRUCTURE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application *is a reissue of U.S. Pat. No. 8,602,773, which issued Dec. 10, 2013 from U.S. patent application Ser. No. 12/447,461, filed Jun. 24, 2009, which* is a national stage application under 35 U.S.C. §371 of PCT Application No. PCT/SE2007/000925 designating the United States, filed on Oct. 18, 2007. The PCT Application was published in English as WO 2008/051142 A1 on May 2, 2008 and claims the benefit of the earlier filing date of Swedish Patent Application No. 0602272-7, filed on Oct. 27, 2006. The contents of PCT Application No. PCT/SE2007/000925, including publication WO 2008/051142 A1, and [Swedish Patent Application No. 0602272-7,] *U.S. Pat. No. 8,602,773* are incorporated herein by reference in their entirety.

*Notice: More than one reissue application has been filed for the reissue of U.S. Pat. No. 8,602,773. The reissue applications are application Ser. No. 14/963,159 (the present application) and Ser. No. 15/400,821, which is a divisional reissue application of application Ser. No. 14/963,159.*

BACKGROUND

1. Field of the Inventions

The present application relates to a dental impression tray for making an impression of a dental structure such as, for example, the dentition of a patient.

2. Description of Related Art

Dental impression trays are used to obtain an impression of a dental structure, such as a patient's dentition. Such impressions can be used, for example, in connection with procedures for making a dental model. A dental impression tray generally includes a tray portion that is contoured to fit over at least a part of a dental structure of which an impression is to be obtained. Such a dental structure may be, for example, a part of a patient's upper or lower dentition. The dental structure may also be, for example, a cast of a patient's dentition.

Techniques for obtaining a dental impression include the single arch and the closed bite technique. In the closed bite technique, a dental impression material is placed in the tray portion and the tray portion is applied to a dental structure such as the dentition of a patient. When the dental impression tray is applied to a patient, the patient will then bite into the impression material to create an impression of the patient's dentition. If the dental structure is a model of a dentition, for example a cast, the dental structure may be pressed into the impression material. Impressions created in this way can be impressions of both a patient's upper and lower dentition. However, it is also possible to make an impression of only the lower dentition or only the upper dentition.

An impression can also be an impression of, for example, only a part of a patient's upper dentition or only a part of a patient's lower dentition. The dental impression can be used for casting a model of the dental structure. As an alternative to using the dental impression for casting a model, a scanning operation can be performed directly on the dental impression itself. Such a procedure is disclosed in U.S. Pat. No. 6,217,334.

In U.S. Pat. No. 5,338,198, a dental modeling simulator is disclosed. As described in that patent, a molded impression of a patient's teeth is taken. The impression is placed on a support table that defines an X-Y plane and a beam of laser light is directed onto the impression to scan the impression with the beam. The scanning is then used to generate a digital image. The tray may be provided with predefined identification marks at upper and lower sides.

SUMMARY

Accordingly, embodiments of the present inventions preferable seek to mitigate, alleviate or eliminate one or more deficiencies, disadvantages or issues in the art, such as the above-identified, singly or in any combination by providing a dental impression tray that can be used to obtain an impression of at least a part of a dental structure such as, for example, the dentition of a patient, a method for making an impression, and a method for making a virtual model according to the appended patent claims.

The present application relates to a dental impression tray for use in obtaining an impression of at least a part of a dental structure such as, for example, the dentition of a patient. As used herein, the term "dental structure" should be understood as including not only dentitions or models thereof, but also structures covered by soft tissue that may be found in the mouth of patients that have lost their teeth and models of such structures.

In some embodiments, the dental impression tray comprises a tray portion adapted to be loaded with impression material. The tray portion is contoured to fit over at least a part of a dental structure (for example a dentition). In some embodiments, the dental impression tray further comprises a handle connected to the tray portion or adapted/shaped to be connected to the tray portion. The handle has a first end at which the handle is connected to the tray portion or adapted to be connected to the tray portion. The handle also has a second end that is a distal end in relation to the tray portion when the handle is connected to the tray portion.

In some embodiments of the invention, the second end of the handle has an edge facing away from the tray portion. In such embodiments, the edge may form a visible line when it is seen from the side facing away from the tray portion. The straight line has a length of at least 30 mm. In some embodiments, the line that is formed by the edge when seen from the side facing away from the tray portion may be a straight line that has a length of at least 60 mm. In some embodiments, the line formed by the edge may have a length of at least 80 mm.

In some embodiments, the handle may be removably secured to the tray portion.

In some embodiments, the handle may comprise two separate parts that are adapted to be connected to each other such that the separate handle parts overlap each other partially, but not completely. In such embodiments where the handle comprises separate parts, the separate handle parts may be adapted to be connected to each other by a snap-on catch formed by the handle parts. However, the connection could also be something else than a snap-on connection. In embodiments where the handle comprises separate parts, the separate parts may be identical in shape. Embodiments are also possible where separate handle parts are not identical in shape.

In embodiments where the handle comprises separate handle parts, each of the separate handle parts may be designed to cooperate with a complementary part of the tray portion in such a way that the handle is locked to the tray portion as long as the separate handle parts are connected to each other.

In some embodiments, the handle may be shaped to define a slot having a length extending at least 30 mm in a direction from the second end of the handle towards the first end of the handle. Such a slot should have a width of at least 10 mm such that objects having a width of up to 10 mm may be moved along the length of the slot.

Possibly, the slot may extend all the way to the edge of the second end of the handle such that the slot divides the edge in two parts.

The tray portion has a shape that defines a cavity with an inner wall. In some embodiments, the dental impression tray may also comprise at least one pad that fits into at least a part of the cavity of the tray portion. In such embodiments, the inner wall may optionally be provided with a first guide structure and the pad may be provided with a second guide structure that fits the first guide structure. Thereby, the first and second guide structures may cooperate with each other. For example, the guide structures may permit the pad to move in the tray portion in a movement guided by the cooperating guide structures and be pressed against a lower part of the tray portion. In this way, the at least one pad can be placed in the tray portion, pushed down guided by the guide structure and finally held in place by the guide structure. The first guide structure may comprise projecting parts forming rails and the second guide structure comprises grooves adapted to receive the projecting parts of the first guide structure. An alternative possibility could be, for example, that the second guide structure comprises rails that interact with grooves in the inner wall.

The pad can be made of many different materials. In some embodiments, the pad is made of an elastic material.

In some embodiments, the tray portion may be contoured to fit over a part of both the upper and lower dentition of a patient and an outer surface of the dental impression tray may be provided with at least one fiduciary marker that can be detected in a scanning operation. Such a fiduciary marker can take many different shapes and may be accomplished in many different ways. In some embodiments, such a fiduciary marker can be made in a material that is opaque to radio waves.

The tray portion may optionally have a wall with a slot to accommodate a patient's upper frenum when the tray portion is fitted over an upper dentition of a patient.

In some embodiments, the dental impression tray may be provided with a machine readable marking such as, for example, an RFID tag. The machine readable marking could also be accomplished in other ways, for example as a bar code.

In some embodiments, the tray portion may be contoured to fit over at least a part of both the upper and lower dental structure of a patient such that an impression can be obtained simultaneously from both the upper and the lower dental structure. In such embodiments, the tray portion may optionally have a holding section with a first side facing in a first direction and a second side placed opposite the first side and facing in a second direction that is opposite to the first direction. Each of the first and second side of the holding section has at least one fastener by means of which the holding section can be locked to a holder having a part with a shape that is complementary in shape to the fasteners on the holding section. The fasteners on both sides of the holding section have the same form such that each side of the holding section can be locked to one and the same holder.

In such embodiments, the holding section may be formed by a projecting part on the tray portion and the fasteners on the opposite sides of the holding section may be shaped by parts of the holding section that define recesses in the holding section. Alternatively, the fastener or fasteners on each side of the holding section may be formed by one or several male elements such as pegs.

In embodiments having a holding section with sides facing in opposite direction and having fasteners on the opposite sides of the holding section, the dental impression tray may further also comprise a handle that can be secured to the tray portion and removed from the tray portion. The handle may then be provided with fastening elements that are complementary in shape to the fasteners on at least one of the opposite sides of the holding section.

In some embodiments, a removable handle for the dental impression tray may comprise at least a first and a second handle part that can be pressed together to form a complete handle. The handle may then optionally have a locking device that can placed in a first position to lock the handle parts to each other and in a second position where the handle parts can be moved away from each other.

The locking device and the first handle part may be shaped such that the locking device is a movable on the first handle part, but cannot be separated from that part. The second handle part may then have a first section corresponding to the second position of the locking device and having such dimensions that the handle parts can be pressed together or moved away from each other when the locking device is in the second position. The second handle part may further have a second section corresponding to the first position of the locking device and having such dimensions that the first and second handle part will be locked to each other when the locking device is placed in its first position and the handle parts are pressed against each other.

In one embodiment, the dental impression tray may form part of a kit used for making a dental impression and holding the impression for a scanning operation. Such a kit may comprise a dental impression tray with a tray portion adapted to be loaded with impression material and contoured to fit over at least a part of both the upper and lower dental structure of a patient such that an impression can be obtained simultaneously from both the upper and the lower dental structure. The tray portion has a holding section with a first side facing in a first direction and a second side placed opposite the first side and facing in a second direction that is opposite to the first direction. Each of the first and the second side of the holding section has at least one fastener by means of which the holding section can be locked to a holder having a part with a shape that is complementary in shape to the fasteners on the holding section. The fasteners on both sides of the holding section have the same form such that each side of the holding section can be locked to one and the same holder. The dental impression tray further comprises a handle that can be secured to the tray portion and removed from the tray portion and the handle is provided with fastening elements complementary in shape to the fasteners on at least one of the opposite sides of the tray portion such that the handle can be secured to the tray portion. The kit further comprises a holder having a part with a shape that is complementary in shape to the fasteners on the holding section of the tray portion and which is identical to the shape of the fastening elements on the handle.

The kit with the dental impression tray and the holder may be used together with scanning equipment in a method for making a dental impression of an upper and a lower dental structure and scanning the impression. In such a method, the handle is secured to the tray portion by means of the fasteners on the holding section and the fastening elements on the handle. The tray portion is loaded with impression material. This can be done after the handle has been secured to the tray portion, but may also be done before the handle has been secured to the tray portion. The tray portion is then placed in the mouth of a patient while the tray portion is guided by means of the handle. An impression is then made of at least a part of the patient's upper and lower dental structure. When the impression has been made, the tray portion is removed from the mouth of the patient and the handle is removed from the tray portion.

The method of making a dental impression and scanning the impression further includes providing a holder having a part that is complementary in shape to the fasteners on the holding section and which is identical to the shape of the fastening elements on the handle. The tray portion is secured to the holder by connecting the first side of the holding section of the tray portion to the holder. A first side of the tray portion is then scanned to obtain a scanning of one of the dental impressions obtained (i.e. an impression of a part of a patient's upper or lower dental structure). The tray portion is removed from the holder and turned 180°. The tray portion is then secured to the holder again which is done by connecting the second side of the tray portion to the holder. After this, a second side of the tray portion is scanned to obtain a scanning of the second dental impression.

It should be emphasized that the term "comprises/comprising" when used in this specification is taken to specify the presence of stated features, integers, steps or components, but does not preclude the presence or addition of one or more other features, integers, steps, components or groups thereof.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures:

FIG. 5b is a front view of the tray portion shown in FIG. 5a.

FIG. 5c is a side view of the tray portion shown in FIG. 5a.

FIG. 6b is a side view of the scanning device shown in FIG. 6a.

FIG. 14a is a top view of another embodiment of a dental impression tray and a pad.

FIG. 14b is a top view of another embodiment of a pad for use in the dental impression tray shown in FIG. 14a.

FIG. 14c is a top view of another embodiment of a dental impression tray and a pad.

FIG. 15a is a side view of the embodiment of the pad shown in FIG. 14a.

DETAILED DESCRIPTION

Figure 1:
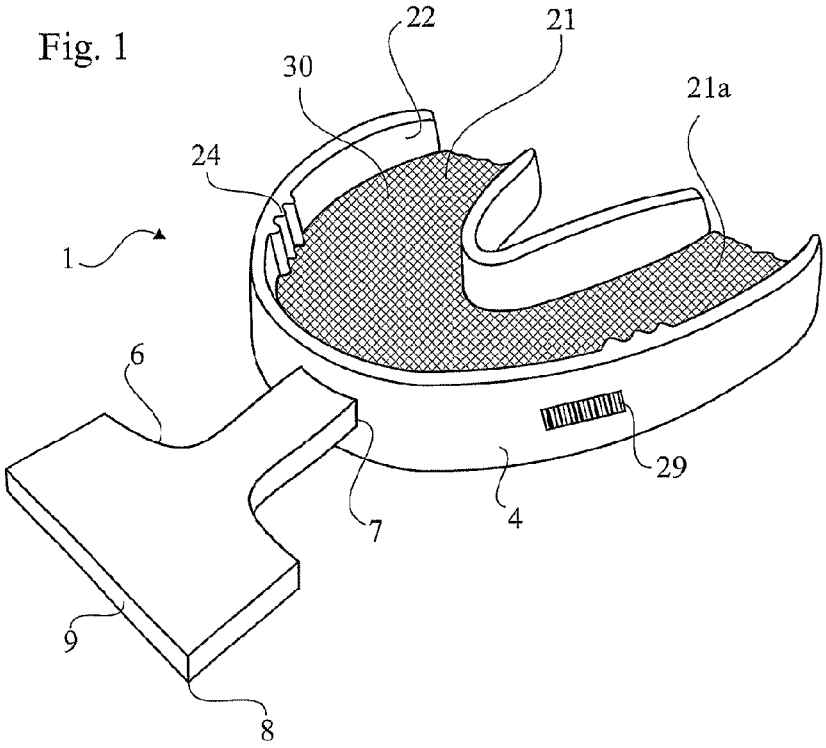
FIG. 1 is a perspective view of a dental impression tray, according to an embodiment of the inventions.

With reference to FIG. 1, a dental impression tray 1 is shown. The dental impression tray can be used to obtain an impression of at least a part of a dental structure such as, for example, the dentition of a patient. The dental impression tray 1 comprises a tray portion 4 adapted to be loaded with impression material. An impression material that can be used with the inventive impression tray 1 may be, for example, a silicon based material. Such impression materials are sold by, for example, 3M ESPE Dental Products, 3M Center, St. Paul Minn., United States. One such material is sold by 3M ESPE under the name IMPRINT™ 3 VPS Impression Material.

The tray portion 4 is contoured to fit over at least a part of a dental structure such as the dentition of a patient. As can be seen in FIG. 1, the dental impression tray 1 further comprises a handle 6 that is connected to the tray portion 4 or adapted to be connected to the tray portion 4. The handle 6 has a first end 7 at which the handle 6 is connected to the tray portion or adapted to be connected to the tray portion 4. The handle 6 also has a second end 8 that is a distal end in relation to the tray portion 4 when the handle 6 is connected to the tray portion 4. The handle 6 can be used to grip the dental impression tray 1 and manipulate the dental impression tray 1 for purposes that will be explained in the following.

Figure 2:
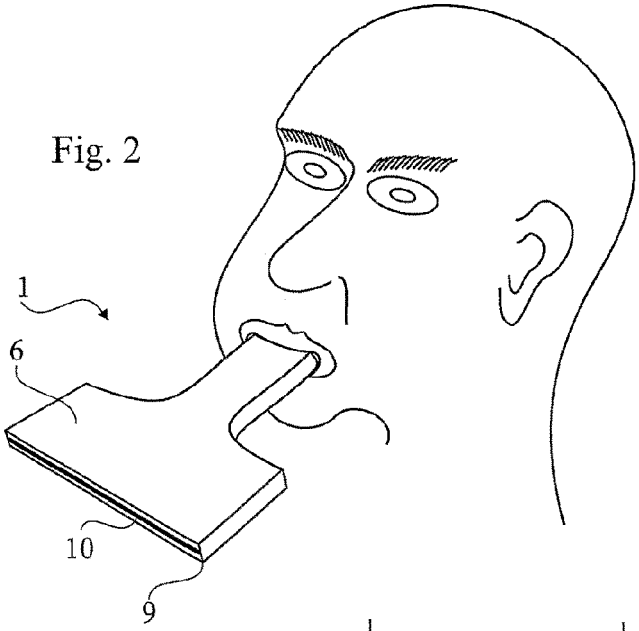
FIG. 2 is a perspective view of a dental impression tray that has been placed in the mouth of a patient.
Figure 4:
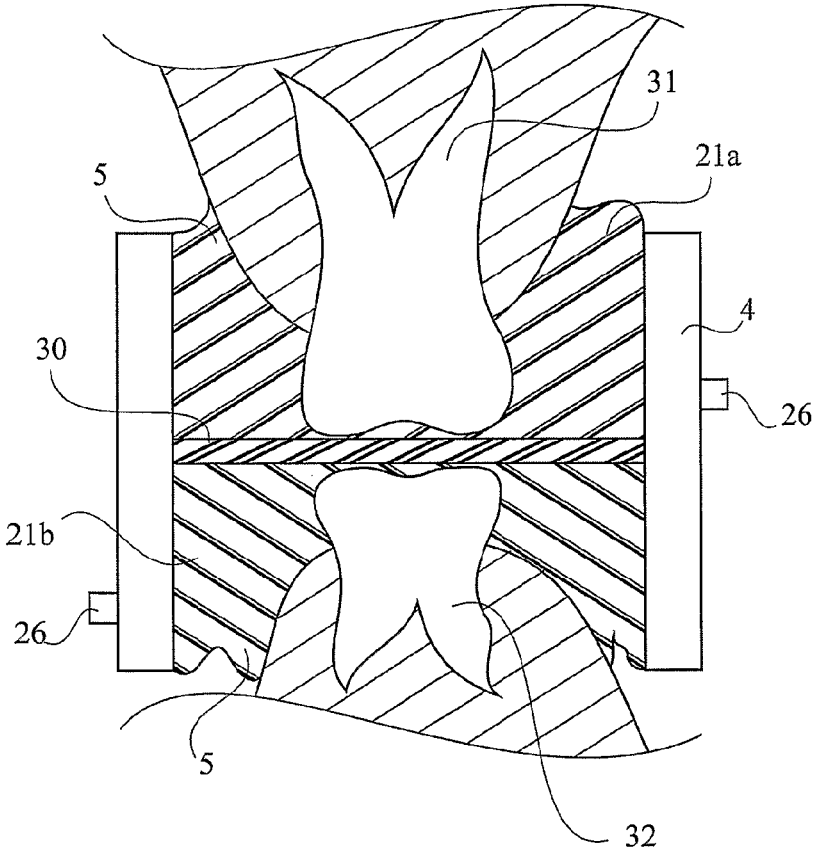
FIG. 4 is a cross-sectional view of an embodiment of a dental impression tray in use when a patient is biting into the tray section to create a dental impression in a dental impression material.

With reference to FIG. 2, it can be seen how the dental impression tray 1 has been placed in the mouth of a patient in order to create an impression of the patient's dentition. In FIG. 2, a patient is biting into the impression material placed in the tray portion 4 of the dental impression tray 1 while the handle 6 remains outside the mouth of the patient. As can be seen in FIG. 4, the tray portion 4 has an inner cavity 21 that may optionally be divided by a partition 30 into an upper cavity 21a and a lower cavity 21b.

It should be understood that, as used herein, the terms "upper cavity" and "lower cavity" refer to what is "upper" and "lower" when the tray portion 4 is located inside the mouth of a patient. The tray portion 4 may very well be designed such that both sides of the tray portion may be applied to both the upper and the lower dentition of a patient. The cavity that is regarded as the "upper" cavity or the "lower" cavity is thus arbitrary. The upper part of the tray portion 4 with its upper cavity 21a can be used to make an impression of an upper dental structure 31, for example an upper dentition 31. A part of the tray portion 4 with its lower cavity 21b can be used to make an impression of a lower dental structure or dentition 32. The partition 30 may be, for example, an elastic fabric such as a rubber fabric 30 or synthetic fabric 30. As can be seen in FIG. 4, the upper and lower cavities 21a, 21b of the tray portion 4 are filled with dental impression material 5 in which an impression is made when the patient bites into the tray section 4, as schematically indicated in FIG. 4.

Figure 6A:
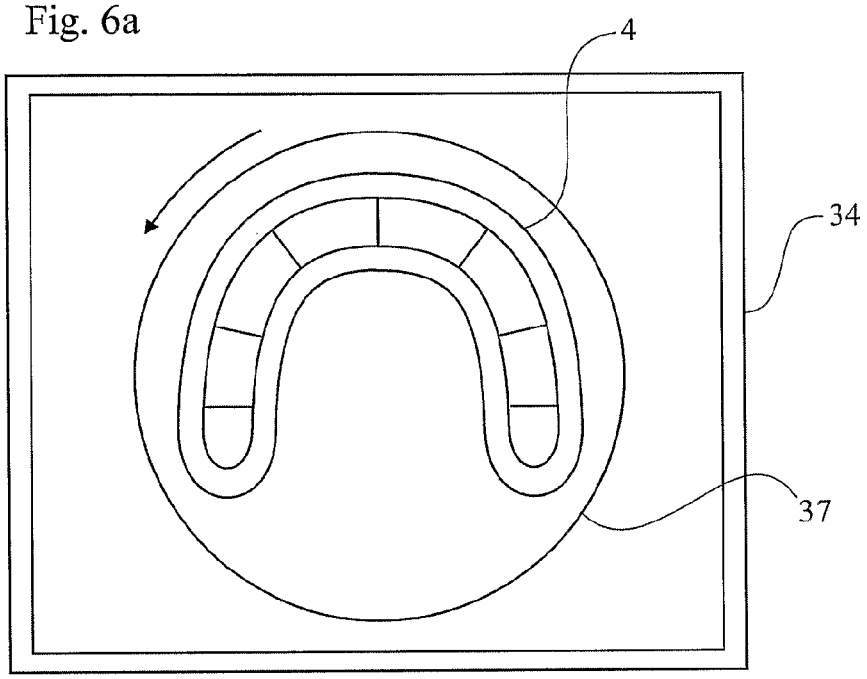
FIG. 6a is a schematic top view illustrating how the tray section of the dental impression tray may be placed in a scanner for a scanning operation, according to an embodiment.
Figure 6B:
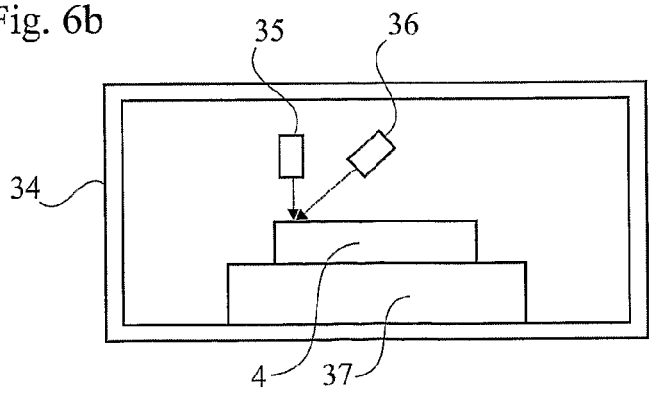

When the patient has bitten into the tray portion 4, the tray portion 4 can be removed from the patient's mouth and placed in a scanning device, as shown in FIGS. 6a and 6b. In the scanning device, a scanning operation can be performed on the impression which is left in the impression material 5 that lies in the tray portion 4. The scanning can be used to create a virtual image or model of the dental structure of which an impression has been made. The scanning operation can be performed, for example, in the way that has been disclosed in U.S. Pat. No. 5,338,198, incorporated herein by reference.

Of course, the impression does not necessarily have to be scanned. A possible alternative to a scanning operation could be, for example, to use the impression as a mould to cast a representation of the dental structure that the dental impression tray has been applied to. In such a casting operation, plaster could be used to create a cast representation of the dental structure in question.

When the dental impression tray 1 is applied to the mouth of a patient in order to create an impression of the dental structure of the patient, it is desirable that the tray portion 4 be positioned correctly such that the impression obtained can be used to create a new dentition that corresponds to a symmetrical bite plane. In this context, the "bite plane" should be understood as a plane where the upper and lower dentitions meet each other when the patient bites.

Figure 3:
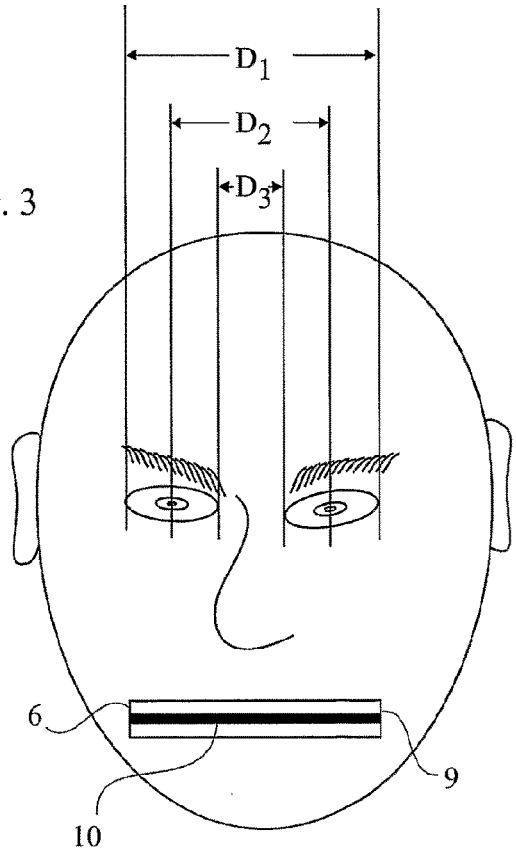
FIG. 3 is a front view corresponding to FIG. 2 and illustrates a principle underlying one of the embodiments.
Figure 8:
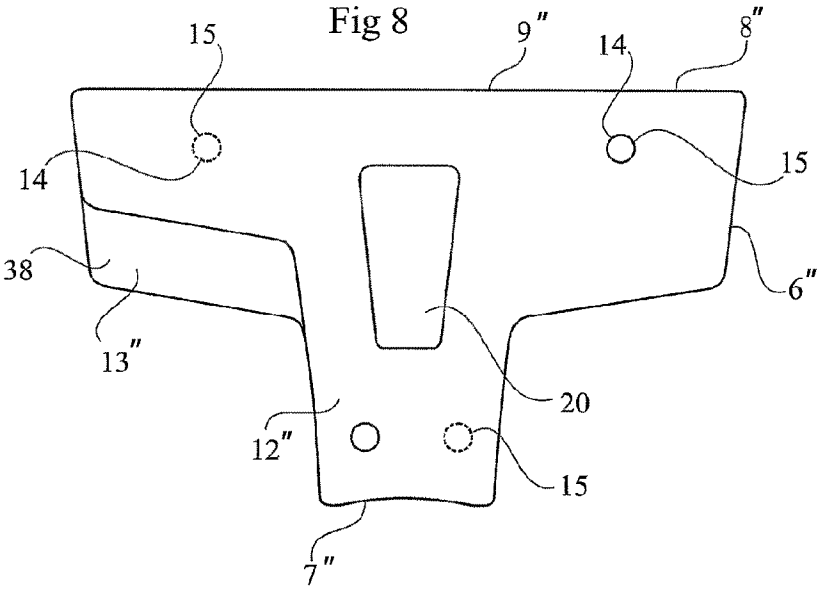
FIG. 8 is a top view of the handle shown in FIG. 7.

One way of achieving the desired symmetry can be to align the handle 6 of the dental impression tray 1 with a feature of the patient's face. This is illustrated in FIG. 1, FIG. 2, FIG. 3 and FIG. 8. With reference to FIG. 1 and FIG. 8, the second end 8 or 8" of the handle 6 or 6" has an edge 9 or 9" that is facing away from the tray portion 4. As can be seen in FIG. 2 and FIG. 3, the edge 9 forms a visible straight line 10 when the edge is seen from the side facing away from the tray portion 4. The edge may optionally be painted or otherwise marked to make the line 10 more easily visible. The edge 9 can be made to be parallel with a plane that divides the upper part of the tray portion 4 from the lower part of the tray portion 4.

In the patient's face, one feature of the patient's face that can be used for alignment is the eyes, i.e. a straight line defined by the patient's own eyes. When the tray portion 4 is correctly positioned in the patient's mouth, the edge 9 of the handle 6 should then be parallel with a straight line between the patient's eyes. The handle 6 allows a user to manipulate the dental impression tray 1 (and thereby also the tray portion 4 that is connected to the handle 6). By gripping the handle 6 and aligning the edge 9 of the handle 6 with the eyes of the patient, the person making the impression can thus ensure that the tray portion 4 is correctly positioned in the patient's mouth.

In FIG. 3, a front view of a patient with a dental impression tray in his mouth is presented. In FIG. 3, the edge 9 of the handle forms a visible straight line 10 to a person who is watching the patient face-to-face. The edge 9 itself may possibly be straight, but could also be curved inwards (i.e. towards the tray portion 4) or outwards (away from the tray portion 4). What matters is only that it appears as a straight line when regarded from the side facing away from the tray portion 4. It should be understood that the edge 9 extends in a plane. The straight line 10 formed by the edge 9 is then visible when it is regarded in the plane in which the edge 9 extends.

The distance between the eyes is, of course, something that varies between different individuals. However, 20-25 mm is a normal value for the closest distance between the eyes of an adult person (the distance between the corners of the eyes closest to the nose). This value corresponds to the distance $D_3$ in FIG. 3. If the length of the straight line 10 is at least 30 mm, it will normally be equal to or larger than the smallest distance between the eyes of an adult person. For this reason, it is considered that the straight line 10 should have a length of at least 30 mm to ensure that it can easily be aligned with the eyes of the patient.

Instead of the shortest distance between the eyes, the length of the straight line 10 could be based on the normal distance between the pupils. For this distance, 60 mm can be mentioned as a representative value for many adult individuals. This value corresponds to the distance $D_2$ in FIG. 3. Alternatively, the length of the straight line 10 may be based on the largest distance between the eyes, i.e. the distance between those corners of the eyes that are most far away from the nose. That corresponds to the distance $D_1$ in FIG. 3. For this distance, 80 mm can be mentioned as a representative approximate value for many adult individuals.

To make the alignment more exact and reliable, the straight line formed by the edge 9 when seen from the side facing away from the tray portion 4 may therefore be given a length of at least 60 mm. To further increase precision in the alignment, the length of the straight line 10 can be chosen to be at least 80 mm.

Figure 11:
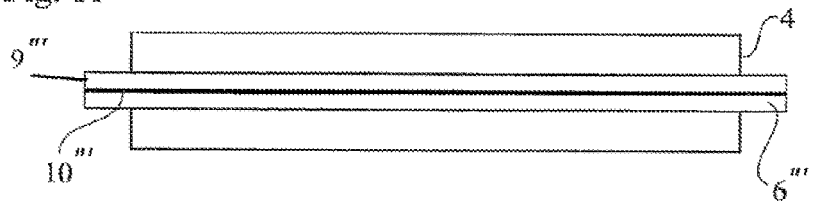
FIG. 11 is a front view of a handle placed on the tray portion, according to an embodiment.

A front view of the entire dental impression tray 1 is shown in FIG. 11 where both the tray portion 4 and the handle 6''' are visible as well as the straight line 10''' formed by the edge 9''' of the handle 6'''.

It should be understood that the edge 9 at the second end 8 of the handle 6 could be shaped in other ways to permit alignment with the feature of the patient's face. For example, it could have an L-shaped form for alignment with the patient's nose and only one of the patient's eyes. The part of the handle that is used to align the tray portion 4 with a part of the patient's facial features could also be located elsewhere than at the second end 8 of the handle 6.

The basic idea behind the embodiment with the edge that forms a straight line can thus be generalized in terms of shaping the handle in such a way that it can be used to align the tray portion 4 with a part of the patient's facial features. The same idea can also be expressed in terms of a method of making an impression in which a part of the handle 6 is used for alignment with a part of a patient's facial features. By gripping the handle 6, and manipulating the dental impression tray 1 such that the straight line 10 becomes aligned with a part of the patient's facial features, the person using the dental impression tray will thereby automatically manipulate the tray portion 4 such that it will be correctly positioned. The method may also be defined more generally as a method for making an impression of at least a part of a patient's dental structure as follows.

The method comprises providing a dental impression tray 1 having a tray portion 4 contoured to fit over at least a part of a dental structure, the dental impression tray 1 further has structure 6 that allows a user of the dental impression tray 1 to manipulate the tray portion 4 when the tray portion 4 is placed in the mouth of the patient. This structure 6 also defines a line 10 that is visible when the tray portion 4 is placed in the mouth of a patient. The tray portion 4 is placed in the mouth of a patient and a comparison is made between the line 10 and a facial feature of the patient. The tray portion 4 is then manipulated until the line 10 becomes aligned with said facial feature of the patient. The structure 6 that allows a user to manipulate the tray portion 4 may be a handle 6 connected to the tray portion (or adapted to allow connection to the tray portion 4). The line 10 may be a straight line 10 that is defined by an edge of the handle 6. Possibly, the line 10 could have some other shape than just a straight line. For example, it could be an L-shaped line that can be aligned with the nose of a patient and an eye of the patient. A straight line can easily be aligned with a straight facial feature such as a line between the eyes. However, the line 10 could optionally be a curved line.

Another embodiment will now be explained with reference to FIGS. 5a-11. With reference to FIG. 6a and FIG. 6b, the dental impression tray 1 can be placed in a scanning device having a chamber 34 where an impression can be scanned. The scanning can be performed by, for example, a laser device such as a line laser device. In FIG. 6b, a laser scanning device is shown schematically that has a laser light source 35 and a detector 36. The tray portion 4 together with an impression of a dental structure (for example a dentition) can be placed on a table, carrier or platform 37 that can perform a rotating movement while the scanning is performed.

When the dental impression tray 1 is placed in the chamber 34 of the scanning device, the handle 6 could present an obstacle. This is especially the case of the dental impression tray 1 is placed on a platform that rotates and the chamber 34 is small. To prevent the handle 6 from causing problems during scanning, it may be desirable to remove the handle 6 from the tray portion 4. To ensure the handle 6 can be quickly and easily removed from the tray portion 4, some embodiments include the use of a handle 6 that is removably secured to the tray portion 4.

Figure 5A:
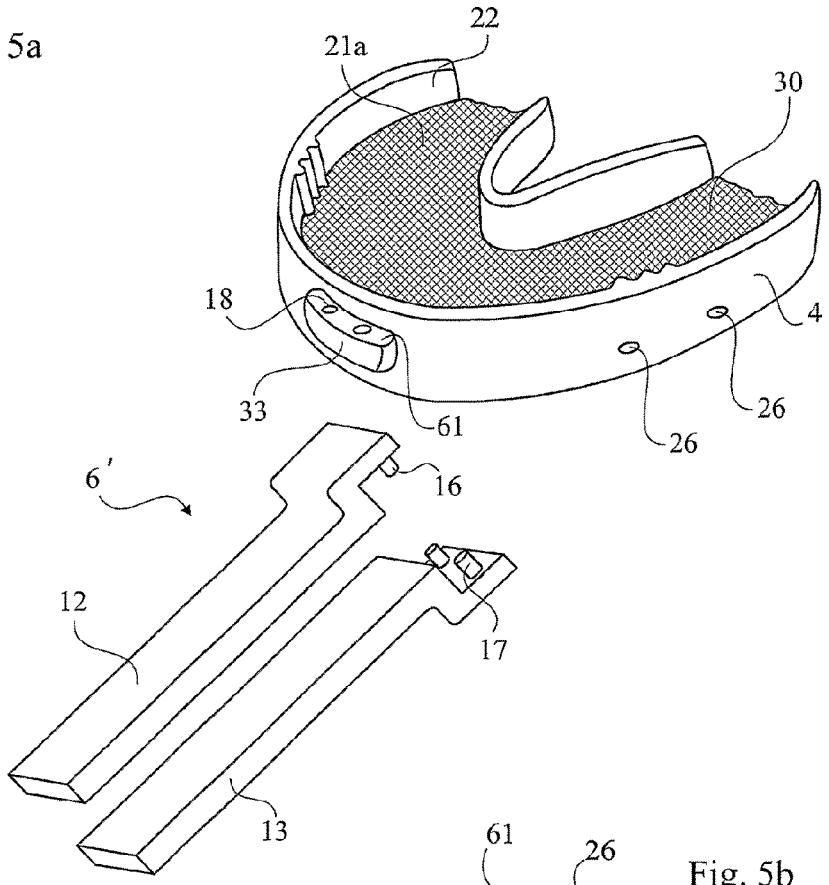
FIG. 5a is a perspective view showing an embodiment where the handle of the dental impression tray can be removed from the tray portion.

With reference to FIG. 5a, an embodiment is schematically illustrated where the handle 6' may be removably secured to the tray portion 4. As shown in FIG. 5a, the handle 6' may have one or several fastening elements 16, 17 adapted to fit one or several corresponding fasteners 18 that may be areas of the tray portion 4 that have been shaped as one or more recesses. The fastening element or elements 16, 17 may be projections, for example, pegs or some other male elements. If the fasteners 18 on the tray portion 4 are shaped as recesses, they may be formed as holes or openings. By pressing the fastening element(s) 16, 17 into such recesses in the tray portion 4, it is possible to secure the handle 6' to the tray portion 4. Of course, the handle 6' can also be removed from the tray portion 4. This can be achieved by removing the fastening element(s) 16, 17 from the recess or recesses in the tray portion.

In FIG. 5a, an embodiment is shown where the fasteners 18 are formed by recess(-es) in a projecting part 33 on the tray portion 4. Of course, it should be understood that such recesses could also be formed elsewhere on the tray portion 4. It should also be understood that, as an alternative, the fasteners 18 on the tray portion 4 may also be formed as projections on the tray portion 4 and be adapted to fit one or several recesses on the handle 6'. The fastening elements 16, 17 would then be formed by areas defining one or more recesses.

Embodiments are possible where the handle 6 is made in one single piece. However, the handle 6 can also be made in more than one piece as indicated in FIG. 5a where the handle 6' comprises two separate parts 12, 13. It should also be understood that the handle 6 may comprise more than two parts.

An embodiment where the handle 6 comprises two separate parts will now be explained with reference to FIGS. 5a-5b and 7-10. As shown in FIG. 5a, the handle 6' for the tray portion 4 may comprise a first and a second part 12, 13 that may be separated. The separate handle parts 12, 13 can be adapted to be connected to each other such that the separate handle parts 12, 13 overlap each other partially, but not completely. This is best seen in FIG. 7 and FIG. 8.

Figure 7:
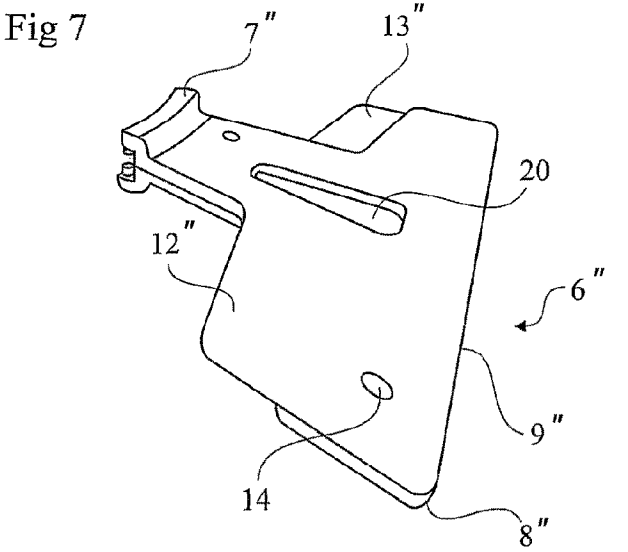
FIG. 7 is a perspective view of an embodiment of a handle.

As indicated in FIG. 7 and FIG. 8, the first and second handle parts 12", 13" are connected to each other in such a way that, when connected, there is a part 38 on each of separate handle part 12", 13" that is not overlapped by the other handle part 12", 13". In FIG. 8, it can thus be seen that the second handle part 13" has a part 38 that is not covered by the first handle part 12". This makes it easy to grip the handle 6" and pull or bend the first and second handle parts 12", 13" apart from each other.

Figure 12:
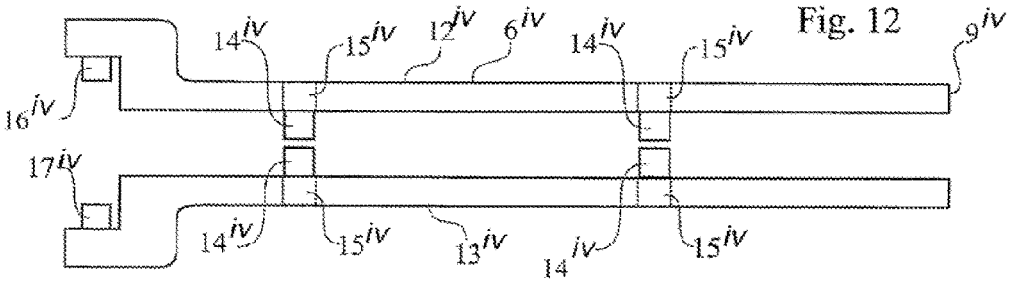
FIG. 12 is a side view of a handle comprising two separate parts that are shown separated from each other, according to an embodiment.

As shown also in, for example, FIG. 7, the handle parts 12", 13" have been connected to each other to form a coherent handle 6". The handle parts 12", 13" may optionally be adapted to be connected to each other by a snap-on catch formed by the handle parts 12", 13". With reference to FIG. 12 and FIG. 8, the snap-on catch may be formed by male elements 14 or $\mathbf{14}^{iv}$ and female parts 15 or $\mathbf{15}^{iv}$ into which the male elements 14 or $\mathbf{14}^{iv}$ may be pressed to a snap fit attachment. The male elements 14 or $\mathbf{14}^{iv}$ may be formed by, for example, pegs. The female parts 15 or 15 may be, for example, openings or through-holes. If the female parts 15 or $\mathbf{15}^{iv}$ are through-holes 15 or $\mathbf{15}^{iv}$, the male elements 14 or $\mathbf{14}^{iv}$ (e.g. pegs) may be visible from the other side. With reference to FIG. 8, it can be seen that pegs 14 have been pressed through holes 15 to be visible from the outside when the handle parts 12", 13" are connected to each other. One way of achieving a snap-on catch may be to design the male elements 14 as conical pegs while the female parts 15 may be holes with a conical shape that corresponds to the conical pegs 14. With reference to FIG. 12, it can be seen that the handle $\mathbf{6}^{iv}$ has handle parts $\mathbf{12}^{iv}$ and $\mathbf{13}^{iv}$ with an edge $\mathbf{9}^{iv}$.

As indicated in FIGS. 7-10, the separate handle parts 12", 13" maybe identical in shape. If they are also unsymmetrical, they will not overlap each other completely when they are put together and connected to each other as indicated in FIGS. 7-10. When the handle parts 12", 13" are put together, they can thus be put together "belly-against-belly" with the back sides facing away from each other. The handle parts 12", 13" will still not overlap each other completely since they are unsymmetrical. If the handle parts 12", 13" are identical in shape, the cost of manufacturing the handle parts can be reduced. Moreover, any two parts 12", 13" can always be connected to each other to form a complete handle 6". However, embodiments are of course also possible where the handle parts 12", 13" are not identical in shape. The handle 6" has a first end 7".

Figure 10:
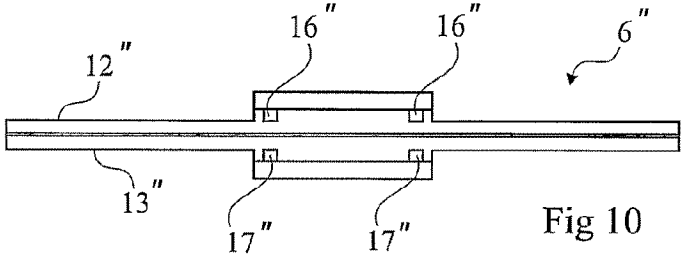
FIG. 10 is a rear view of the handle shown in FIG. 7.
Figure 9:
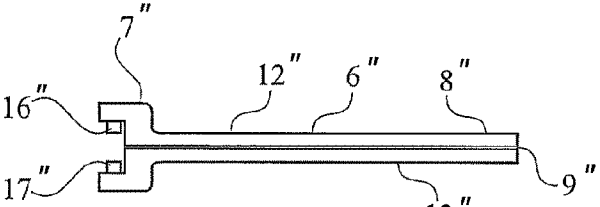
FIG. 9 is a side view of the handle shown in FIG. 7.

As shown in for example FIG. 9 and FIG. 10, each of the separate handle parts 12", 13" may be provided with fastening element 16", 17", for example, some kind of projection/male element that can cooperate with a complementary fastener 18 on the tray portion 4, e.g., a part shaped to define a recess as explained previously with reference to FIG. 5a. When the separate handle parts 12", 13" are connected to each other by a snap connection, the handle 6" is locked to the tray portion 4 as long as the separate handle parts 12", 13" are connected to each other. The handle parts 12", 13" may be held together by the snap connection and the fastening elements 16", 17" that connect the handle 6" to the tray portion 4 will thus be held in place until the first and second handle parts 12", 13" are separated from each other.

The idea of using a removably secured handle 6 can be combined with the idea of using a handle that can be used for alignment with a facial feature of a patient. However, it can also be used independently of how the handle is otherwise designed.

The idea of using a tray portion with a removably secured handle, e.g., 6' or 6" in FIGS. 5a and 7, may also be defined in terms of a method in which a dental impression is made, the handle 6' or 6" removed from the tray portion 4 and the tray portion 4 placed in the scanning device and scanned.

The dental impression tray 1 may optionally be packaged with the handle 6' or 6" disconnected from the tray portion 4. This can make the dental impression tray 1 shorter to make it fit into a smaller space, e.g. for purposes of packaging.

While the idea of using a removable handle 6 has been described above, it should be understood that embodiments are conceivable that have a handle 6 that is fixedly connected to the tray portion 4. For example, the handle 6 can be made in one piece with the tray portion 4.

Another embodiment will now be explained with reference to FIG. 13a. In some cases, the person handling the dental impression 1 tray may prefer to keep the handle 6 on the tray portion 4. This may be the case, for example, if the dental impression tray 1 is used to cast a plaster model of the impression. The same situation applies if the handle is not detachable. In such cases, the dentist or dental technician may want to use the dental impression tray 1 together with existing equipment that may interfere with the handle $\mathbf{6}^{v}$. One way of solving this problem may be to provide a slot in the handle $\mathbf{6}^{v}$.

Figure 13A:
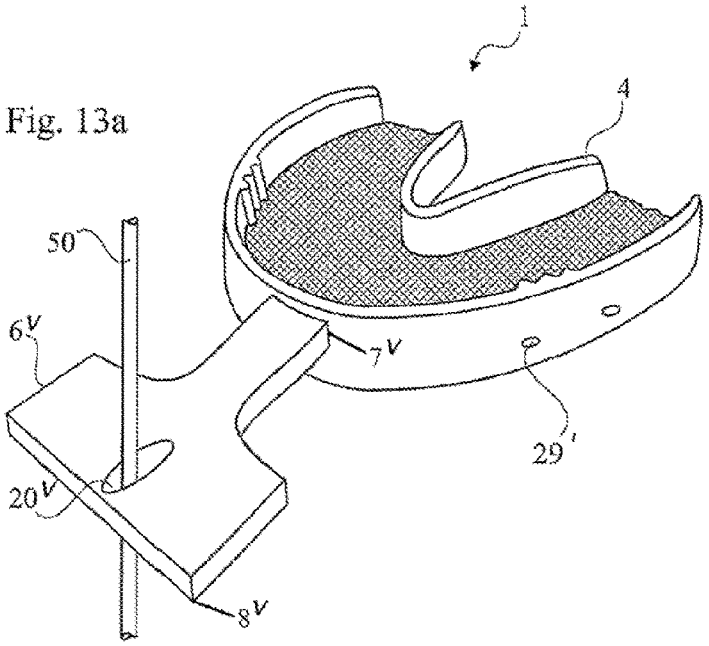
FIG. 13a is a perspective view of an embodiment of a dental impression tray which is adapted for use in combination with an incisal pin, according to an embodiment.

As can be seen in FIG. 13a, the handle $\mathbf{6}^{v}$ may be shaped to define a slot $\mathbf{20}^{v}$. Components of existing equipment may include, for example, an incisal pin 50 for an articulator. An incisal pin in an articulator is typically used to adjust the distance between an upper and a lower model of a dentition. Incisal pins for articulators may typically have a diameter of up to 10 mm and it should be possible to move the handle relative to such objects at least 20 mm. Therefore, the length of the slot $\mathbf{20}^{v}$ may be chosen such that it extends at least 30 mm in a direction from the second end $\mathbf{8}^{v}$ of the handle $\mathbf{6}^{v}$ towards the first end $\mathbf{7}^{v}$ of the handle $\mathbf{6}^{v}$.

The slot $\mathbf{20}^{v}$ may be given a width of at least 10 mm such that objects having a width of up to 10 mm (e.g. incisals for articulators) maybe moved along the length of the slot $\mathbf{20}^{v}$.

Figure 20:
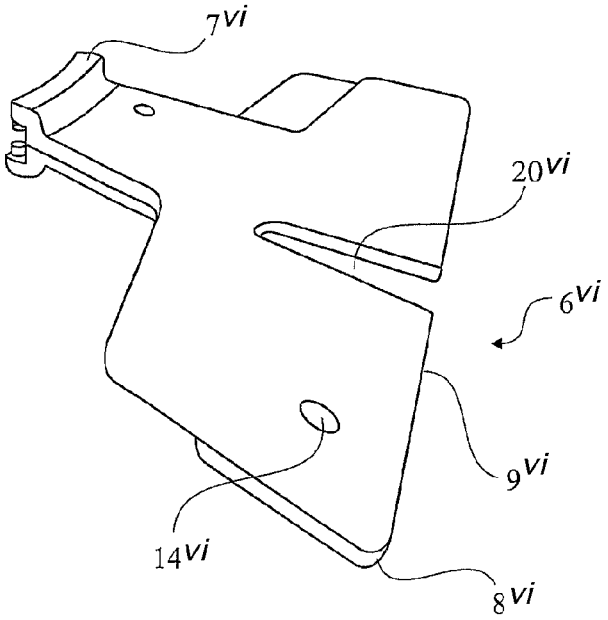
FIG. 20 is a perspective view of another embodiment of a handle.

In a different embodiment shown in FIG. 20, the slot $\mathbf{20}^{vi}$ extends all the way to the edge $\mathbf{9}^{vi}$ of the second end $\mathbf{8}^{vi}$ of the handle $\mathbf{6}^{vi}$ such that the slot $\mathbf{20}^{vi}$ divides the edge $\mathbf{9}^{vi}$ in two parts. As a result, the handle $\mathbf{6}^{vi}$ can more easily be made to fit such objects as the rod 50 shown in FIG. 13a. The handle $\mathbf{6}^{vi}$ has a first end $\mathbf{7}^{vi}$ and a male element $\mathbf{14}^{vi}$.

Figure 13B:
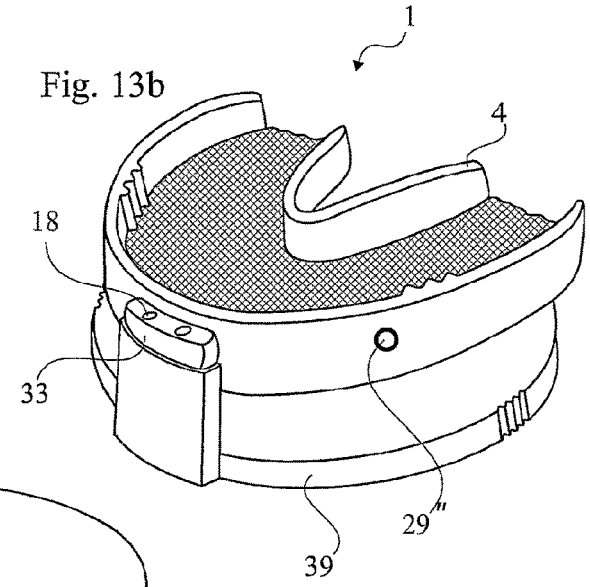
FIG. 13b is a perspective view of a dental impression tray being mounted on a holder, according to an embodiment.
Figure 13C:
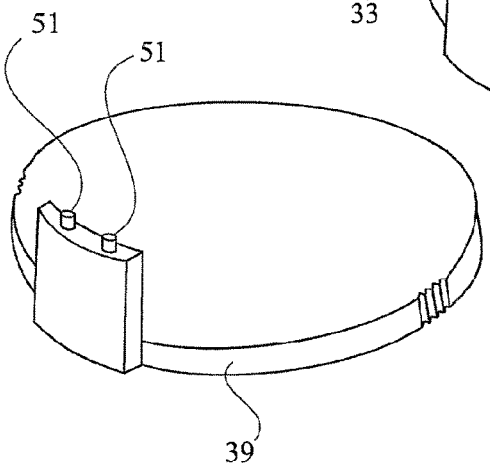
FIG. 13c is a perspective view of the holder shown in FIG. 13b.

Another embodiment is shown in FIG. 13b and FIG. 13c. In FIG. 13b, it is shown how the handle 6 has been removed from the tray portion 4 as a preparation for a scanning operation. The tray portion 4 has been placed on a holder 39. As shown in FIG. 13c, the holder 39 has a part 51 with a shape that is complementary to the in shape to the fasteners 18 on the holding section 33 of the tray portion 4.

In the embodiment shown in FIGS. 13b and 13c, the holding section 33 is formed by a projecting part on the tray portion 4. The part 51 of the holder 39 that is complementary in shape to the fasteners 18 maybe shaped to define male elements such as pegs. Such male elements or pegs can fit the corresponding fasteners 18 on the holding section 33 when these fasteners 18 are areas of the holding section 33 shaped as recesses. When the male elements of the holder 39 are pressed into the recesses of the holding section 33, the tray portion 4 is secured to or held by the holder 39. The holder 39 can be placed in a scanning device and support the tray portion 4 during the scanning operation. The holder 39 together with the tray portion 4 can then be placed on, for example, such a carrier 37 as is indicated in FIG. 6b. Since the holder 39 is designed to cooperate with the same holding section 33 as the handle 6, the equipment according to the embodiment of FIG. 13b and FIG. 13c is versatile and easy to use. It is not necessary to have any separate recess or other element on the tray portion 4 to fasten it to the holder 39. The part 51 of the holder 39 that is complementary in shape the fasteners 18 on the tray portion 4 may thus be male elements having a shape that is similar to or identical to the shape of the fastening elements $\mathbf{16}^{iv}$, $\mathbf{17}^{iv}$ shown in FIG. 12.

With reference to FIGS. 13b-13d and FIGS. 6a and 6b, yet another embodiment and further variations will now be explained in the following. A possible method for making a dental impression of an upper and a lower dental structure and scanning the impression may be as follows. A tray portion 4 is provided that is contoured to fit over at least a part of an upper and lower structure of a patient. The tray portion may have a holding section 33 which may be projecting from the rest of the tray portion 4 as in FIG. 5a, but could also be designed in other ways such that it does not project from the rest of the tray portion. The holding section 33 has a first side 61 (see also FIGS. 5b and 5c) facing in a first direction and a second side 62 (see FIGS. 5b and 5c) opposite to the first side 61 and facing in a second direction that is opposite to the first direction. Each of the first and second side 61, 62 of the holding section 33 has at least one fastener 18 that may be an area of the holding section 33 that is shaped as a recess. The fasteners 18 on both sides 61, 62 of the holding section 33 have the same form. A handle 6' may be provided that can be secured to and removed from the tray portion 4. The handle 6' has fastening elements 16, 17 that are complementary to the fasteners 18 on at least one of the opposite sides 61, 62 of the holding section 33. The handle 6' is secured to the tray portion 4 by means of one or several of the fasteners 18 on the holding section 33 and one or several fastening elements 16, 17 on the handle 6'. The tray portion 4 is loaded with impression material, either before or after the handle 6' is secured to the tray portion 4.

When the tray portion 4 is loaded with impression material and the handle 6' is secured to the tray portion 4, the tray portion 4 is placed in the mouth of the patient and an impression is made of at least a part of the patient's upper and lower dental structure. During this part of the procedure, the handle 6' may optionally be used to guide the tray portion 4.

After an impression has been made of the upper and lower dental structures, the tray portion is removed from the mouth of the patient. The handle 6' is removed from the tray portion 4, either before or after the tray portion 4 is removed from the mouth of the patient. The tray portion 4 is then secured to a holder 39. The holder 39 has a part that is complementary in shape to the fasteners on the holding section 33 and it is identical in shape to the fastening elements 16, 17 on the handle 6'. The tray portion 4 is secured to the holder 39 by means of connecting the first side of the tray portion 4 to the holder 39. A first side of the tray portion 4 is then scanned such that a scanning of one of the dental impressions is obtained, i.e. a scanning of either the impression of the upper dental structure or the lower dental structure. At the same time, a part of the surface of the tray portion 4 itself will of course be scanned.

Figure 13D:
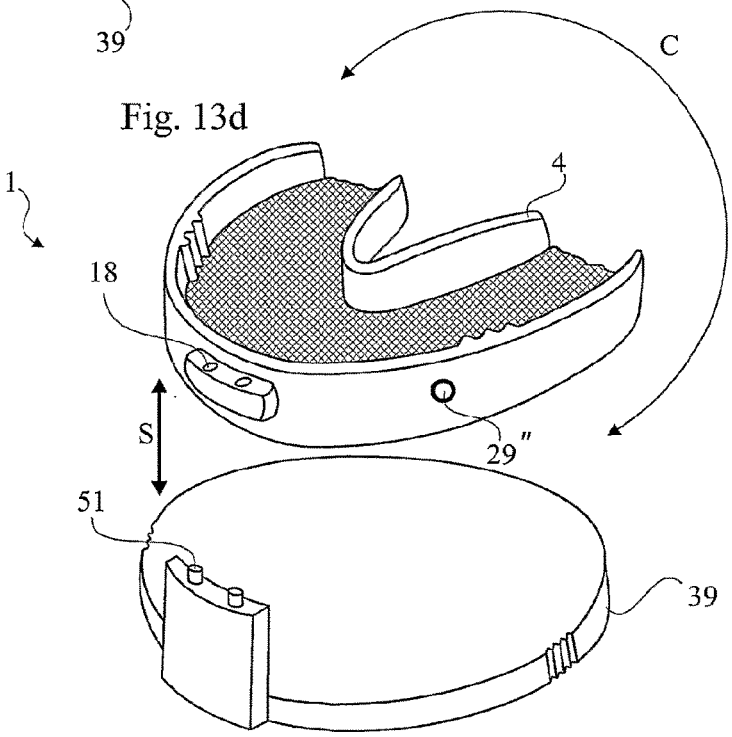
FIG. 13d is a perspective view of the impression tray and the holder shown in FIG. 13b, illustrating how the tray may be removed from the holder and turned 180°, according to an embodiment.

The tray portion is then removed from the holder as indicated symbolically by arrow S in FIG. 13d and turned 180° as symbolically indicated by arrow C in FIG. 13d. The tray portion 4 is then once again secured to the holder 39 by means of connecting the second side of the tray portion to the holder 39. After this, the second side of the tray portion 4 is scanned to obtain a scanning of the second dental impression as well as a further scanning of the tray portion 4. This method entails that a scanning can easily be obtained of both the upper and the lower dental structure of a patient and, at the same time, of the tray portion 4. The fact that the tray portion 4 itself is also scanned can be used to match the scannings of the dental impressions with each other as will be explained in more detail with reference to FIGS. 4 and 17.

It should be understood that the dental impression tray that is used for the above-described method may optionally be provided both with and without a removable handle 6. Embodiments are thus possible that include only a tray portion 4 adapted to be loaded with impression material and contoured to fit over at least a part of both the upper and lower dental structure 31, 32 of a patient such that an impression can be obtained simultaneously from both the upper and the lower dental structure 31, 32 while a scanning of the tray portion 4 is also obtained which can later be used to match the scanning of the lower dental structure with the scanning of the upper dental structure. However, if the dental impression tray is to be used in combination with a holder 39 that holds the dental impression tray during scanning of both sides of the dental impression tray, the tray portion 4 of the dental impression tray should have a holding section 33 with a first side 61 facing in a first direction and a second side 62 placed opposite the first side 61 and facing in a second direction that is opposite to the first direction.

Moreover, each of the first and second side 61, 62 of the holding section 33 should have at least one fastener by means of which the holding section can be locked to a holder 39 having a part with a shape that is complementary in shape to the fasteners on the holding section 33. The fasteners on both sides of the holding section should then have the same form. When the fasteners on both sides of the holding section have the same form, this entails that each side of the holding section can be locked to one and the same holder.

As previously explained with reference to FIG. 5a, the holding section 33 may optionally be formed by a projecting part on the tray portion 4 while the fasteners 18 on the opposite sides 61, 62 of the holding section 33 may be shaped by parts of the holding section 33 that define recesses in the holding section 33.

In case the dental impression tray 4 comprises a removable handle 6', the handle 6' shall be provided with fastening elements 16, 17 that are complementary in shape to the fasteners on at least one of the opposite sides of the holding section 33. Such a removable handle may be designed, for example, as shown with reference to FIGS. 7-12 or as shown in FIGS. 22-35, but a suitable removable handle could also be designed in other ways.

One embodiment may also take the form of a kit for making a dental impression and holding the impression for a scanning operation. Such a kit may comprise a dental impression tray having a holding section 33 and a removable handle 6' with fastening elements 16, 17 as described previously and a holder 39 having a part with a shape that is complementary in shape to the fasteners 18 on the holding section 33 of the tray portion. When a holder 39 is included that has a part with a shape that is complementary to the fastener or fasteners 18 on each side on the holding section 33 of the tray portion 4, this entails that the tray portion 4 can easily be placed in a position for scanning both sides of the tray portion 4 and thereby obtain a scanning of both the upper and lower dental structure of a patient. When the handle parts 12, 13 have fastening elements 16, 17 identical in shape to the part 51 of the holder 39 that is complementary in shape to the fasteners 18 on the tray portion 4, this entails that the tray portion 4 can be easily fitted to both the handle 6' and the holder 39.

Yet another embodiment will now be explained with reference to FIGS. 14a-17. Some patients may lack teeth completely. If a patient has been without teeth for a long period, the jawbone itself may regress. If the patient is then asked to bite in the dental impression tray 1, the patient may fail to bite together completely since the regression of the jaw bone has gone too far. As a consequence, the dental impression obtained may be insufficient. The embodiment shown in FIGS. 14a-17 has been designed to deal with that problem.

With reference to FIG. 14a, the tray portion 4 has a shape that defines a cavity 21 with an inner wall 22. The dental impression tray 1 further comprises at least one pad 23 that fits into at least a part of the cavity 21 of the tray portion 4. A side view of the at least one pad 23 is presented in FIG. 15a. Optionally, the inner wall 22 may be provided with a first guide structure 24 and the pad 23 can be provided with a second guide structure 25 that fits the first guide structure 24. The first and second guide structures 24, 25 may then cooperate with each other in a way that permits that the pad 23 is pressed down into the tray portion 4 in a movement guided by the cooperating guide structures 24, 25. The at least one pad 23 is then held securely by the cooperating guide structures 24, 25. A side view of the pad 23 is presented in FIG. 15a.

Figure 15A:
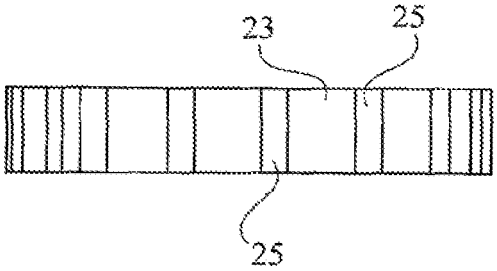
Figure 16:
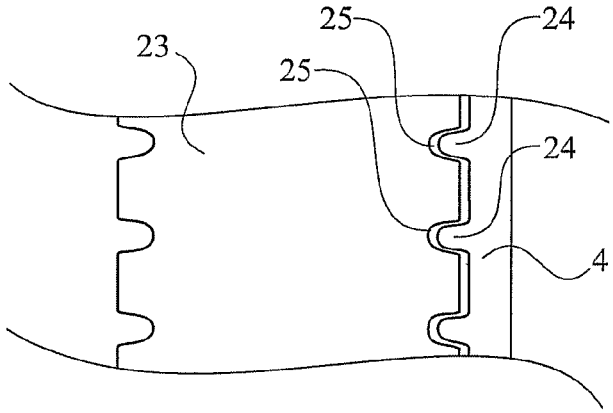
FIG. 16 is a schematic top view illustrating how the pad shown in FIG. 15a can cooperate with a respective dental impression tray, according to an embodiment.

The first guide structure 24 may comprise projecting parts forming rails 24 and the second guide structure 25 may comprise grooves 25 adapted to receive the projecting parts of the first guide structure 24. This embodiment is shown in FIGS. 14a and 15a. Alternatively, the pad 23 may have projecting elements that fit grooves in the inner wall 22 of the tray portion 4. The guide structures 24, 25 can cooperate with each other (engage each other) as indicated in FIG. 16.

Figure 15B:
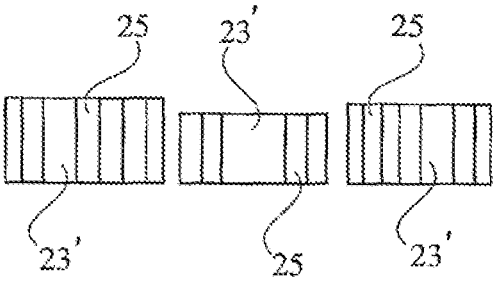
FIG. 15b is a side view of an embodiment of a pad that is substantially similar to the embodiment shown in FIG. 14b.

In FIG. 14b, an embodiment is illustrated where not one pad 23 is used, but three separate pads 23'. A side view of such an arrangement is illustrated in FIG. 15b. In some embodiments, one pad is used for taking an impression of the upper jaw whereas several pads are used for taking an impression of the lower jaw. Hence, greater flexibility is achieved.

With reference to FIG. 14c, an embodiment is shown that is basically similar to the embodiment of FIG. 14b. However, this embodiment is without the projecting parts 24 and grooves 25 A side view of such an arrangement is illustrated in FIG. 15c.

Figure 15C:
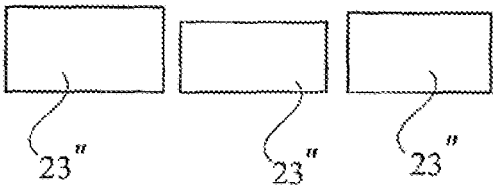
FIG. 15c is a side view of an embodiment of a pad that is substantially similar to the embodiment shown in FIG. 14c.

It will be noted that, in the embodiments shown in FIG. 15b and FIG. 15c, the different pads 23' or 23" are of different heights. For example, in FIG. 15b, the pad 23' that is located in the middle (the second pad from the left) is lower than the first pad from the left. The reason for this will be explained in the following.

Figure 17:
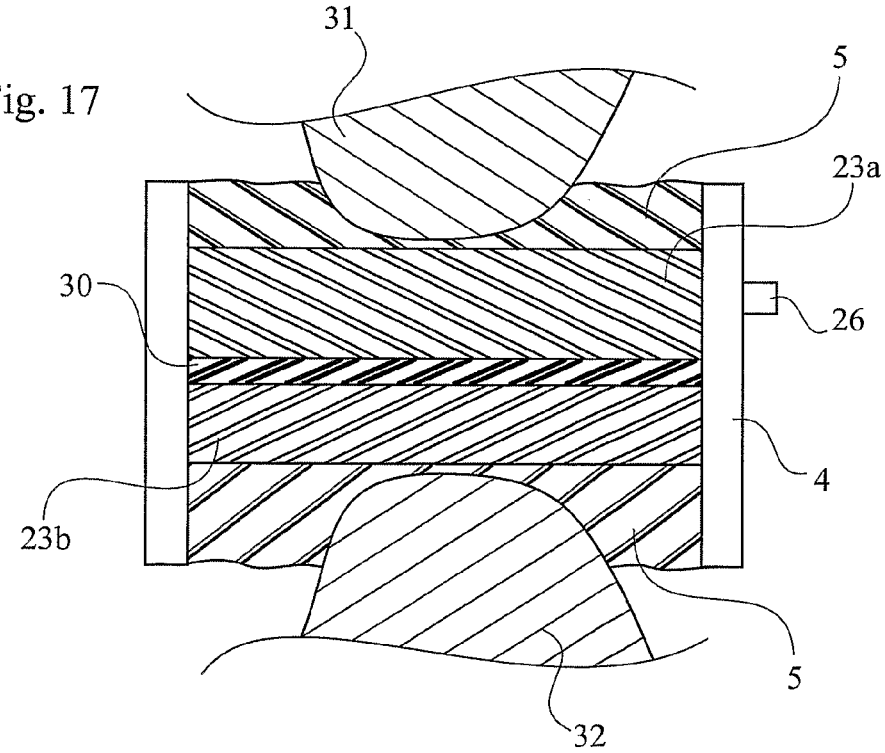
FIG. 17 is a cross-sectional view similar to FIG. 4 and gives a schematic illustration of how the embodiment of FIG. 14 can be used to get an impression on a patient who has no teeth at all, according to an embodiment.

When a pad 23 is placed in the cavity 21 of the tray portion 4, the dental impression tray 1 will be more suitable for a person whose jaw bone has regressed. FIG. 17 presents a cross-sectional schematic illustration of a dental impression tray applied to a patient completely lacking teeth and having suffered regression of the jaw bone. A first pad 23a and a second pad 23b have been placed in the tray portion 4 and secured in the tray portion in such a way that they reach the partition 30.

In FIG. 17, the first pad 23a is placed in an upper part of the tray portion 4 while the second pad 23b is placed in a lower part of the tray portion 4 (in this context, it should be understood that "upper" and "lower" refers to how the tray portion is placed in the mouth of a patient). As indicated in FIG. 17, the upper dental structure 31 lacks teeth. This is also the case with the lower dental structure 32. In spite of this, the patient is still able to bite together properly thanks to the pads 23a, 23b that have been placed in the tray portion 4. The impression material 5 has been placed over the pads 23 and the patient can now bite directly into the impression material 5 which he or she might have been unable to do without the pads 23. In FIG. 17, an embodiment with two pads 23a, 23b is illustrated (an upper pad 23a and a lower pad 23b). It should be understood that embodiments with only an upper pad 23a may be possible or embodiments with only a lower pad 23b. This may be dependent on the dental structure of the individual patient. As can be seen in FIG. 17, the partition 30 separates the upper part of the tray portion 4 from the lower part of the tray portion 4. It should be understood that, as an alternative to the guide structures 24, 25 that are illustrated in FIGS. 14a and 16, the pads 23 can be held in the tray portion 4 by an adhesive material, such as an adhesive tape or glue, that secures the pads to the partition 30 or the inner wall 22 of the tray portion. The adhesive tape could be a double-sided adhesive tape.

In FIGS. 14a and 15a, the pad 23 is shown as a single piece, i.e., a single upper pad 23a or a single lower pad 23b. However, it should be understood that, for both the "upper" part of the tray portion 4 (it should be understood that "upper" refers only to what is "upper" when the tray portion 4 is placed in the mouth of a patient) and the "lower" part of the tray portion 4, the pad 23 may be divided into several parts that are separate from each other as indicated in FIGS. 14b, 14c, 15b, 15c. On, for example, the upper dentition of a patient, it may be desirable to apply more than one pad 23.

For example, it could be desirable to apply one pad 23 to a left part of the patient's upper dentition and another pad 23 to the right part of the patient's dentition. In such a case, two pads 23 may be used. One can also imagine cases where three pads 23 are used on the upper or lower dentition of a patient. For example, one separate pad 23 could be used on a front part of a dentition while two other pads are used to the left and right side of the patient's dentition. Of course, embodiments are also conceivable where four, five or even more pads 23 are used on the upper or lower dentition. Embodiments are also possible where a pad 23 is designed to be used on just a part of a patient's upper or lower dentition. For example, a pad 23 could be designed to be applied to only the left part of the patient's upper dentition or the front part of the patient's lower dentition.

If the patient's jawbone has suffered regression, it may be the case that the regression of the jawbone has not been equally damaging to all parts of the jawbone. It may thus be the case that some parts of the patient's jawbone have suffered very extensive regression while other parts have suffered only mild regression. For this reason, pads 23 of different height may be used. For example, let's assume that the left and right parts of a patient's upper jaw bone have suffered serious regression, but that the front part of the upper jawbone has suffered only a mild regression. A dental technician or dentist can then place relatively high pads in the left and right part of the tray portion 4 while a low pad is placed in the front part of the tray portion 4. The height of each pad 23 depends on the degree of regression of the jaw bone at the place the pad 23 will be put to use. When the patient bites together, it will thus be possible for the dentist or dental technician to get a correct impression in the impression material and to get the distance between the upper and lower jaw right. A solution with more than one pad 23 may be applied in both the upper and lower jaw (and thus on both sides of the partition 30).

It should be understood that, regardless of whether one or several pads 23 are used, the pad(s) 23 does not necessarily fill the entire cavity 21 of the tray portion 4. If a special guide or holding structure 24 is used, it is possible that the pad(s) 23 cooperate(s) with guide structure 24 on only a part of the inner wall 22. In some embodiments, the pad(s) 23 could cooperate with guide structure 24 on only the front part of the inner wall 22, i.e. the part adjacent the handle 6. In that embodiment, it may be so that the pad(s) 23 is not even in contact with the rear part of the inner wall 22.

In some embodiments, the pad 23 can be made of an elastic material such as, for example, rubber. A material such as rubber is gentle if it should come into contact with the tissue in the mouth of a patient without teeth. Alternatives to rubber may also include, for example, synthetic materials. However, embodiments having a pad made of a more rigid material are also conceivable. Furthermore, the pad 23 can be made of a material that is relatively easy to adjust the shape of. Than, each pad can be precisely adjusted to fit a specific patient. Such adjustable material is e.g. rubber or plastic material.

The guide structures 24, 25 help to secure the pad(s) 23 to the inner wall 22 of the tray portion when the pad(s) is (are) placed in the tray portion 4. However, embodiments are conceivable where the pad 23 and the inner wall 22 of the tray portion 4 lack guide structure. As an alternative to the term "guide structure," the projections 24 and grooves 25 may be called "fastening structure" or "holding structure."

Figure 18:
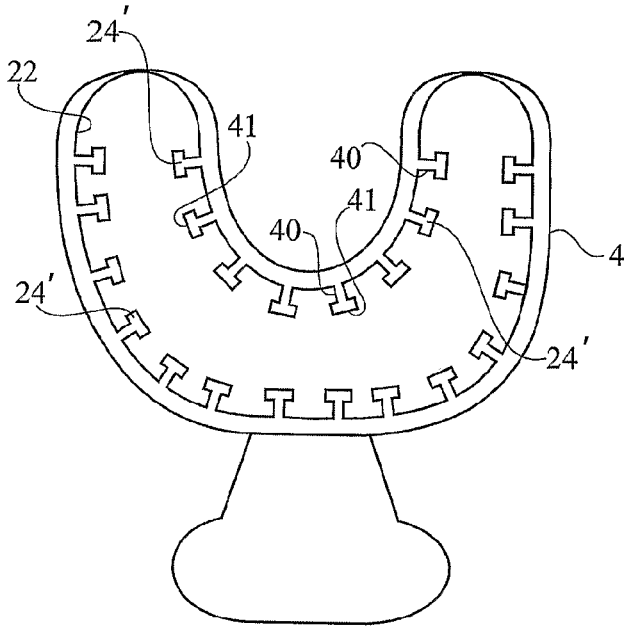
FIG. 18 is a top view of another embodiment of a dental impression tray.

The guide structure 24 on the inner wall of the tray portion 4 can also serve a different function, namely to prevent undesired movement of the impression material 5. The guide structure 24 tends to lock the impression material against such movement. The inner wall 22 of the tray portion 4 may thus be provided with such a structure independently of whether a pad 23 as described above is used or not. FIG. 18 illustrates an alternative shape of the guide structure 24. The shape indicated in FIG. 18 may be used to interact with a pad 23, but can be used separately for the purpose of preventing the impression material 5 from being moved in an undesired way. As indicated, in FIG. 18, the guide structure 24' may be formed by relatively thin projecting parts 40 that end with a thicker head 41. In FIG. 18, a guide structure 24' is shown along the entire periphery of the inner wall 22. However, embodiments are also possible where only a part of the inner wall 22 is provides with such elements. For example, embodiments are possible where only that part of the inner wall 22 that is adjacent the handle 6 is covered by such a guide structure.

It should be understood that the idea of using a pad 23 that fits the tray portion 4 can be combined with all other embodiments disclosed in this application. For example, the use of a pad 23 in combination with a handle that can be aligned with a patient's facial features further improves the possibility of obtaining a correct impression that can be used for making a successful dental restoration. However, the idea of using a pad could also be used independently of how the dental impression tray 1 is otherwise designed. For example, it could be used independently of the shape of the handle 6. Conceivably, it could also be used in embodiments where the dental impression tray 1 does not have a handle.

The idea of using a pad for certain patients, e.g., patients suffering from regression of the jaw bone, can also be defined in terms of a method for making dental impressions, in which method a dental impression tray 1 with at least one pad is inserted into the mouth of such a patient and an impression formed.

Figure 19:
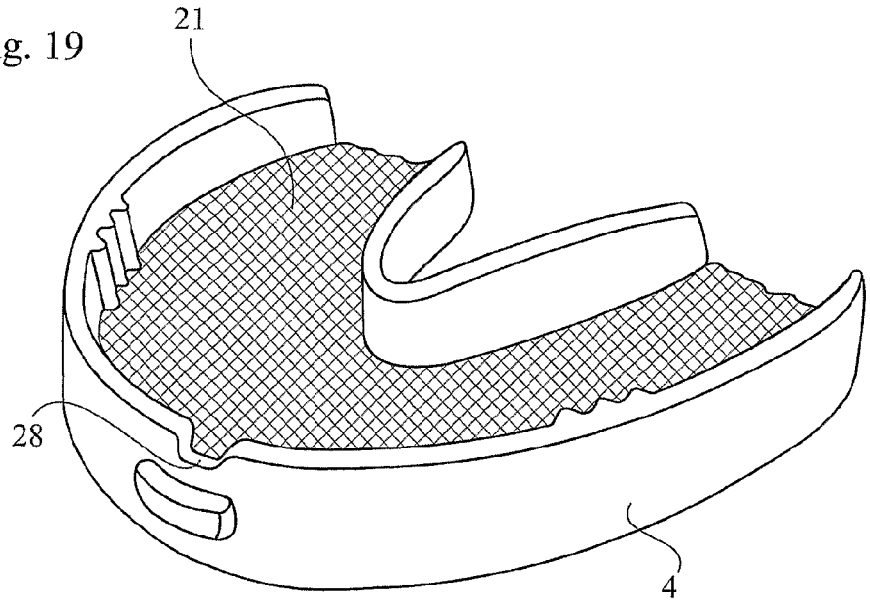
FIG. 19 is a top view of yet another embodiment of a dental impression tray.

Another embodiment will now be explained with regard to FIG. 19. As indicated in FIG. 19, the tray portion 4 may have in its wall a slot 28 to accommodate a patient's upper frenum when the tray portion 4 is fitted over upper dentition 31 of a patient. This makes the dental impression tray 1 more comfortable for the patient. It should be understood that the embodiment of FIG. 19 is entirely optional, but that it may be used independently of how the dental impression tray 1 is otherwise designed. It can thus be used in combination with other embodiments shown or it can be used in isolation. Conceivably, the idea could be used independently of whether the dental impression tray is provided with a handle or not.

Figure 21:
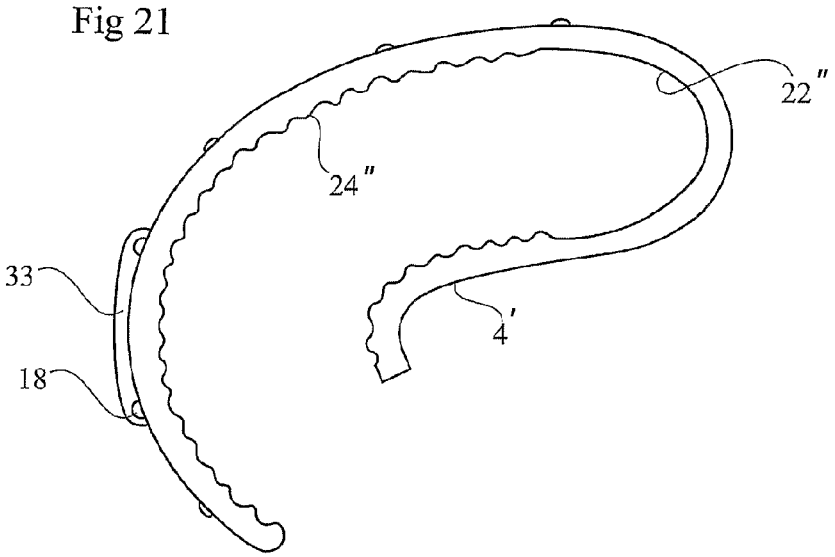
FIG. 21 is a view from above of yet another embodiment of a dental impression tray.

With reference to FIG. 21, it should be noted that the tray portion 4' does not necessarily have to be designed to extend along the entire upper or lower dental structure of a patient, but could be designed to extend along only a part of a patient's upper or lower dental structure, e.g, as shown as 4', wherein the tray portion 4' has an inner wall 22" and a guide structure 24".

Another optional feature will now be explained with reference to FIG. 4 and FIG. 17. The tray portion 4 can be designed to fit over only an upper or a lower dental structure (or a part of such a structure). However, it can be designed and contoured to fit over a part of both the upper and lower dental structure or dentition 31, 32 of a patient. When this is the case, an impression can simultaneously be obtained from both the upper and the lower dental structure. It is then desirable that one can match the upper impression with the lower impression. To this end, an outer surface of the dental impression tray 1 may be provided with at least one fiduciary marker 26 that can be detected in a scanning operation. When the dental impression tray 1 is subsequently scanned, the upper and lower impressions may be scanned separately. When the result of the scanning is fed to a computer, the at least one fiduciary marker can serve to match the scanning of the upper dental structure with the scanning of the lower dental structure. The fiduciary marker 26 can be included in the scanning of both the upper impression and the lower impression and it can thus serve as a reference point such that the scanning of the upper impression can be correctly combined with the scanning of the lower impression. Instead of only one fiduciary marker, several fiduciary markers 26 can be used. For example, there may be two, three, four or five fiduciary markers 26 or even more than five fiduciary markers 26. The fiduciary markers may optionally have some special form to facilitate identification, e.g. square, triangular or round.

Figure 5B:
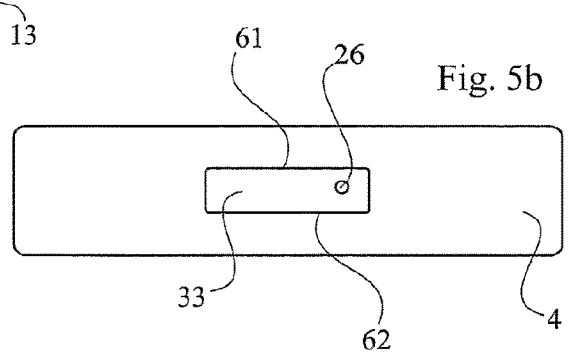
Figure 5C:
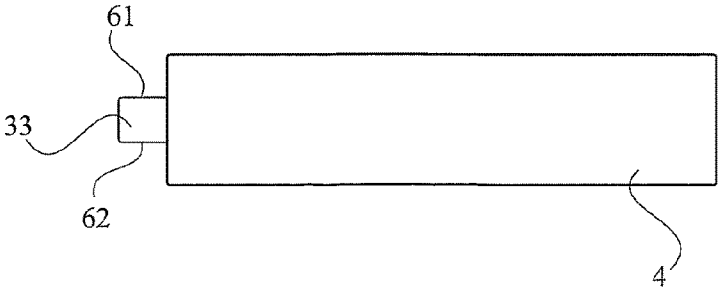

With reference to the embodiments shown in FIGS. 5a-c and FIGS. 13b-c, it should be understood that fiduciary markers 26 may be placed on the holding section 33 of the tray portion 4. As previously explained, the holding section 33 may be shaped as a projecting part on the tray portion 4. When one or several fiduciary markers 26 are placed on such a projecting part, this may be helpful when an upper and a lower impression are have been scanned and the scannings are to be matched with each other. In FIG. 5b, it is indicated how a fiduciary marker 26 has been placed on the holding section 33 of a tray portion 4. Some parts of the holding section 33 can be scanned both when the upper dental impression and the lower dental impression are scanned. In particular, one or several fiduciary markers 26 may be scanned in both scannings. Since also the tray portion 4 and the fiduciary marker (or markers) 26 thereon are scanned, this can be used to match the scannings of the dental impressions with each other.

In some embodiments, the at least one fiduciary marker 26 can be made in a material that is opaque to radio waves. This can be useful if the scanning is done as, for example, a CT scanning (computer tomographic scanning). In such a scanning operation, X-ray is used. If the at least one fiduciary marker 26 is opaque to radio waves, it can then be detected during such a scanning operation. A CT scanning may be performed in, for example, the following way.

Firstly, a dental impression tray 1 is placed in the mouth of a patient after dental impression material has been placed in the tray portion 4. The patient bites into the dental impression material. A CT scanning is performed while the dental impression tray is still in the mouth of the patient. The jaw bone of the patient will be visible in the scanning together with the at least one radiopaque fiduciary marker 26. It will thus be possible to see how the jaw bone is located in relation to the fiduciary marker 26. The dental impression tray 1 is then removed from the patient's mouth. A scanning is now performed on either the upper or lower dental impression obtained in the dental impression material. Also in this scanning, the at least one fiduciary marker 26 will be included. The dental impression that has been scanned can then be linked to the fiduciary marker 26. The dental impression tray 1 can then be turned over and the dental impression on the other side is scanned. Once again, the at least one fiduciary marker 26 is included in the scanning. The data from the separate scanning operations is then fed into a computer. Through the at least one fiduciary marker 26 that is radiopaque, the results of the three scanning operations can be linked to each other.

It should be understood that the idea of using fiduciary markers 26 can be combined with all other embodiments described. For example, the use of at least one fiduciary marker in combination with the idea of using a part of the handle to align the tray portion 4 with a part of the patient's facial features can help improve precision when an impression is made. However, the idea of using one or several fiduciary markers can also be used independently of how the dental impression tray 1 is otherwise designed. For example, it can be used independently of how the handle 6 is designed. Conceivably, it could also be used on dental impression trays that do not have a handle 6.

It should be understood that the idea of using one or several fiduciary markers 26 can be defined in terms methods for making an impression. For example, the idea of using at least one fiduciary marker 26 made in a radiopaque material could be defined in terms of a method where X-ray is used for the scanning operation.

Another embodiment will now be explained with reference to FIG. 1 and FIG. 13a. When a large number of impressions are made and/or handled, there is a risk that different impressions are mixed up, i.e. confused with each other. To prevent that, a dental impression tray 1 can be provided with a machine readable marking 29 or 29'. The machine readable marking comprises a coding that is unique for each patient. The coding can be applied at the same occasion as the impression is made and linked in, for example, a computer memory, to the patient from whom the impression has been obtained. The machine readable marking may be, for example, a bar code as indicated in FIG. 1. However, in another embodiment, the machine readable marking 29 comprises an RFID (Radio Frequency Identification) tag 29' as symbolically indicated in, for example, FIG. 13a. An RFID tag provides for, inter alia, quick and reliable identification. An example of RFID technology is disclosed in, for example, U.S. Pat. No. 7,053,775, incorporated herein by reference. Another example of RFID technology is disclosed in U.S. Pat. No. 7,009,526, incorporated herein by reference. Yet another example of RPID technology is disclosed in U.S. Pat. No. 6,693,539, incorporated herein by reference.

The embodiment including the machine readable marking 29 could also be understood in terms of a method including the steps of making an impression with a dental impression tray 1, marking the dental impression tray with a machine readable marking and linking the marking to a unique patient. The idea may also be defined in terms of a system that comprises a computer loaded with data linking various individual dental impression trays to individual patients. Such a system might also comprise a plurality of dental impression trays where individual trays have machine-readable markings linked to the data in the computer. The system may also comprise at least one reader for the machine-readable markings 29, for example, a reader for RFID tags or a bar code scanner.

It should be understood that the idea of using a machine-readable marking 29, can be combined with all embodiments described in this application. For example, the idea can be combined with the embodiment where a pad 23 is used or it can be combined with the idea of using a removably secured handle 6. However, it should also be understood that it is an idea that can be used independently of how the dental impression tray 1 is otherwise designed. For example, it could be used independently of how the handle 6 is designed and independently of whether the dental impression tray 1 has a handle or not.

Yet another embodiment will now be explained with reference to FIGS. 22-35. A dental impression tray 1 may be designed such that the handle $\mathbf{6}^{vii}$ comprises at least a first and a second handle part $\mathbf{12}^{vii}$, $\mathbf{13}^{vii}$ that can be pressed together to form a complete handle $\mathbf{6}^{vii}$ while the handle $\mathbf{6}^{vii}$ has a locking device 52 that can placed in a first position to lock the handle parts $\mathbf{12}^{vii}$, $\mathbf{13}^{vii}$ to each other and in a second position where the handle parts $\mathbf{12}^{vii}$, $\mathbf{13}^{vii}$ can be moved away from each other.

Figure 22:
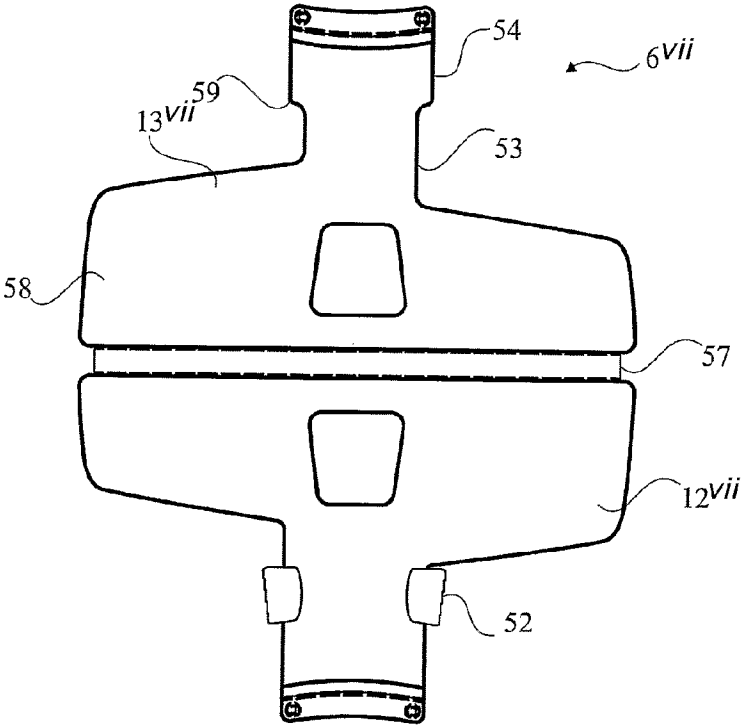
FIG. 22 is a top view showing yet another embodiment of a handle for a dental impression tray, the handle comprising two handle parts.
Figure 24:
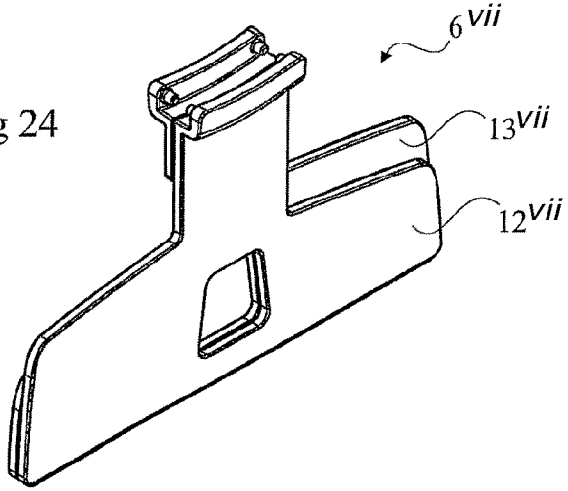
FIG. 24 is a perspective view of the handle shown in FIG. 22 in a state where two handle parts have been placed together to form the handle, according to an embodiment.
Figure 26:
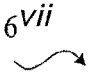
FIG. 26 is a side view of the handle shown in FIG. 24.
Figure 26:
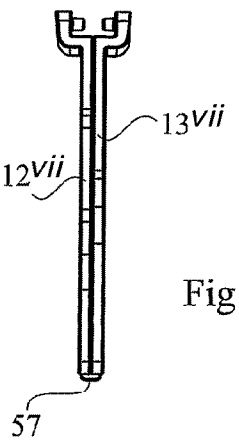
Figure 25:
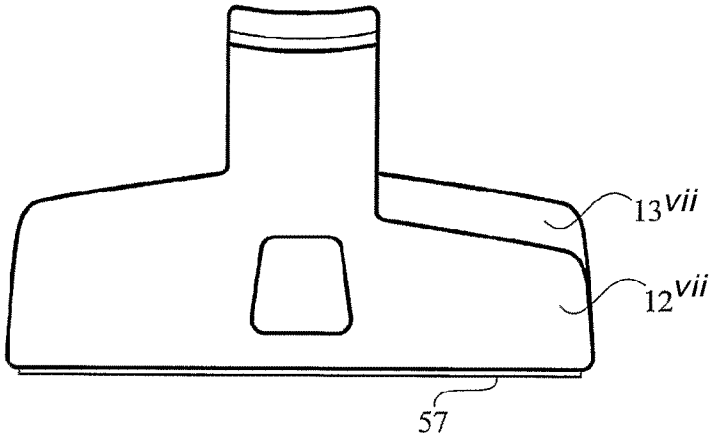
FIG. 25 is a top view of the handle shown in FIG. 24.
Figure 29:
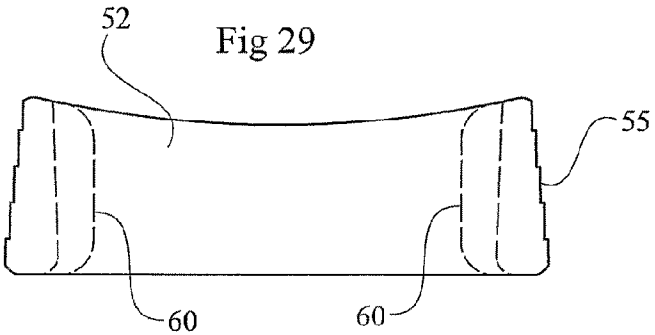
FIG. 29 is a top view of the locking device shown in FIG. 27.
Figure 30:
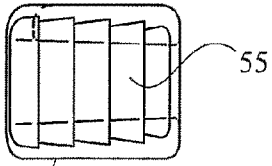
FIG. 30 is a side view of the locking device shown in FIG. 27.

As illustrated in FIG. 22, the handle $\mathbf{6}^{vii}$ may be formed by two handle parts $\mathbf{12}^{vii}$, $\mathbf{13}^{vii}$. These parts $\mathbf{12}^{vii}$, $\mathbf{13}^{vii}$ can be combined to form the handle $\mathbf{6}^{vii}$ as indicated in FIG. 24, FIG. 25 and FIG. 26. Each handle part $\mathbf{12}^{vii}$, $\mathbf{13}^{vii}$ may be divided into a grip part 58 and a bridging part 59 for connection to the tray portion 4. In FIG. 22, it is indicated that the handle parts $\mathbf{12}^{vii}$, $\mathbf{13}^{vii}$ may optionally be linked to each other at their grip parts 58 by a flexible strip 57 that can optionally be formed in one piece with the handle parts $\mathbf{12}^{vii}$, $\mathbf{13}^{vii}$. The material may be, for example, a plastic material and the flexible strip 57 may be much thinner than the handle parts $\mathbf{12}^{vii}$, $\mathbf{13}^{vii}$ in order to ensure that the flexible strip 57 can be bent easily (i.e. that it is flexible) such that the handle parts $\mathbf{12}^{vii}$, $\mathbf{13}^{vii}$ can be folded together.

In the embodiment of FIGS. 22-35, the handle parts $\mathbf{12}^{vii}$, $\mathbf{13}^{vii}$ are not adapted to be connected to each other by a snap-on catch as in the embodiment shown in FIGS. 8 and 12. Instead, the handle parts $\mathbf{12}^{vii}$, $\mathbf{13}^{vii}$ can be connected to each other in another way that will now be explained with reference to FIGS. 22-35.

As can be seen in FIG. 22, the handle parts 12$^{vii}$, 13$^{vii}$ are not identical. The second handle part 13$^{vii}$ has, on its bridging part 59, a first section 53 that is relatively narrow and a second section 54 that is relatively wide, i.e. wide compared to the first section 53. The corresponding area of the first handle part 12$^{vii}$ is not divided in this way. On the bridging part 59 of the first handle part 12$^{vii}$, a locking device 52 has been placed as can be seen in for example FIGS. 22 and 23. A possible design of the locking device 52 is shown in FIGS. 27-30.

Figure 27:
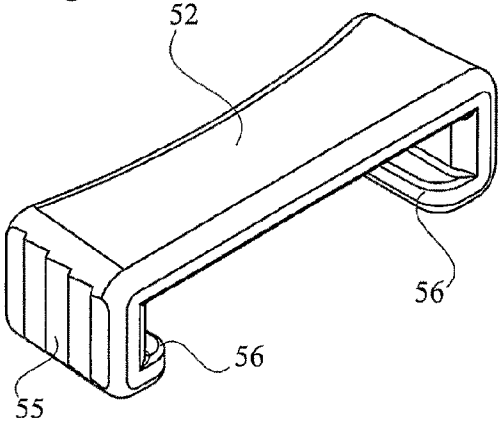
FIG. 27 is a perspective view of a locking device designed to lock together the handle parts of the handle shown in FIGS. 22-26, according to an embodiment.
Figure 28:
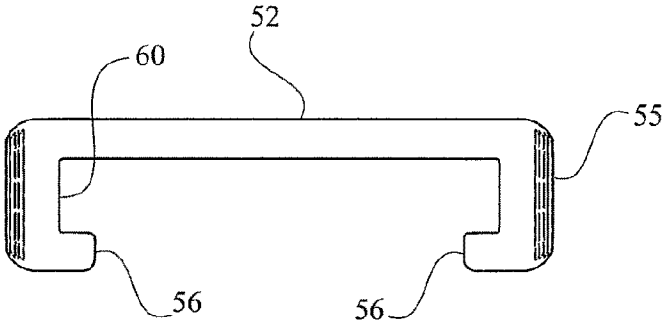
FIG. 28 is a front view of the locking device shown in FIG. 27.

As indicated in FIG. 27 and in FIG. 28, the locking device 52 may have the shape of a beam with hooks 56 at the ends of the beam. The hooks 56 can be used to hold the handle parts 12$^{vii}$, 13$^{vii}$ of the handle 6$^{vii}$ together. On an external surface of the locking device 52, the locking device 52 is provided with a high friction part 55 that can be achieved through, for example, a serrated or uneven surface. The high friction part 55 may of course also be achieved by other means. An internal wall 60 of the locking device 52 will face the perimeter of the handle parts 12$^{vii}$, 13$^{vii}$ when the locking device holds the handle parts 12$^{vii}$, 13$^{vii}$ together.

It should be understood that the idea of using a special locking device as shown in FIGS. 22-35 for holding two handle parts together could be combined with other embodiments, for example, a handle having an edge that forms a visible straight line. However, the idea of using a locking device 52 as shown in FIGS. 22-35 may also be put to use for all embodiments having a removable handle formed by different handle parts 12, 13, regardless of how the dental impression tray is otherwise designed. The locking device 52, as exemplified in FIGS. 22-23 and FIGS. 27-35, entails that the handle parts 12$^{vii}$, 13$^{vii}$ can be easily connected to each other in a reliable way and just as easily separated from each other.

If one of the handle parts is made with a narrow section 53 as shown in FIG. 22, this entails that it will be easier for the locking device 52 to be moved between a first position where it holds the handle parts 12$^{vii}$, 13$^{vii}$ together and a second position where the handle parts 12$^{vii}$, 13$^{vii}$ can be separated from each other.

If the locking device 52 is permanently locked on one of the handle parts 12$^{vii}$, 13$^{vii}$, this entails that it is immediately available and that it is not easily lost.

The locking device 52 and the first handle part 12$^{vii}$ are shaped such that the locking device 52 is a movable on the first handle part 12$^{vii}$ but cannot be separated from that part. One way of achieving this may be to make the bridging part 59 of the first handle part 12$^{vii}$ so wide that the locking device 52 cannot be separated from the first handle part 12$^{vii}$ without deformation of either the first handle part 12$^{vii}$ or the locking device 52 (or both). In other words, the distance between the tips of the hooks 56 is always smaller than the width of the first handle part 12$^{vii}$. As a consequence, the locking device 52 is permanently locked to the first handle part 12$^{vii}$.

Figure 23:
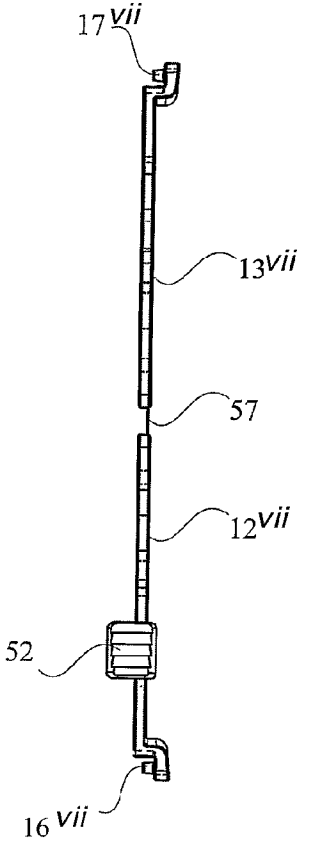
FIG. 23 is a side view of the embodiment of the handle shown in FIG. 22.
Figure 31:
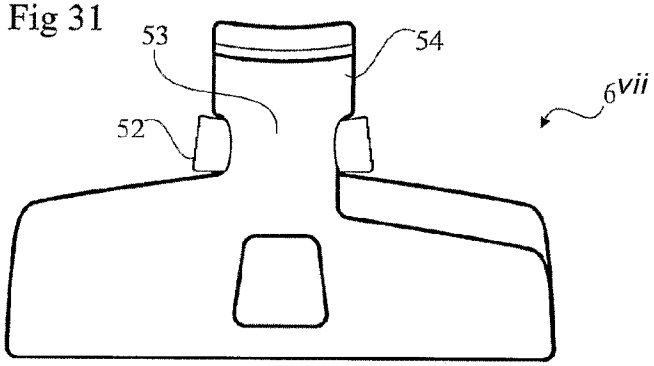
FIG. 31 is a perspective view of the handle shown in FIG. 22, but wherein the handle parts are put together and not yet locked to each other by a locking device, according to an embodiment.

In FIG. 22 and in FIG. 23, it can be seen how the locking device 52 is placed on the first handle part 12$^{vii}$. In this position of the locking device 52, the handle parts 12$^{vii}$, 13$^{vii}$ can be pressed tightly against each other without being impeded by the locking device. The reason is that this position of the locking device 52 matches the narrower first section 53 of the second handle part 13$^{vii}$. With reference to FIG. 31, it can be seen how the handle parts 12$^{vii}$, 13$^{vii}$ have been pressed together while the locking device 52 is still in the same position as in FIGS. 22 and 23. In this position, the locking device 52 does not lock the handle parts 12$^{vii}$, 13$^{vii}$ to each other since the locking device contacts the second handle part 13$^{vii}$ at its narrow section 53 where the hooks 56 of the locking device do not extend over the handle part 13$^{vii}$.

Figure 32:
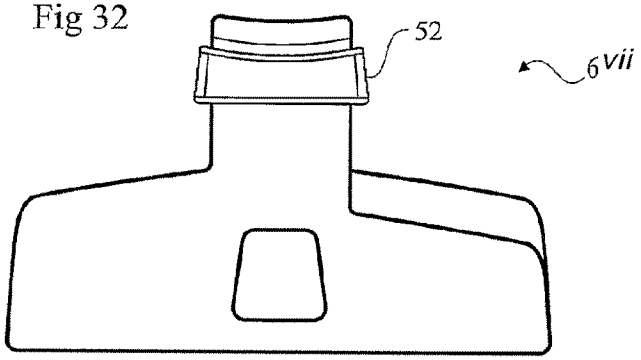
FIG. 32 is a perspective view of the handle shown FIG. 31, from the other side of the handle and with a locking device placed in a position to lock the handle parts to each other, according to an embodiment.
Figure 34:
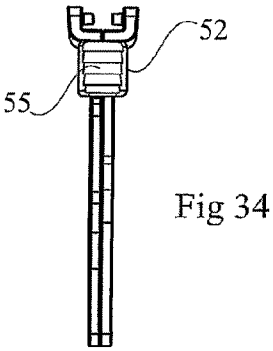
FIG. 34 is a side view of the handle and locking device shown in FIGS. 32 and 33.

Reference will now be made to FIG. 32. In FIG. 32, the locking device 52 has been moved to a position where the locking device 52 is placed over the second section 54 of the second handle part 13$^{vii}$. The second section 54 is wider than the first section 53 and the hooks 56 of the locking device will now extend over the second handle part 13$^{vii}$ such that the handle parts 12$^{vii}$, 13$^{vii}$ are locked to each other. This position can also be seen in perspective in FIG. 33 and from the side in FIG. 34. This position of the locking device is a first position where the locking device locks the handle parts 12$^{vii}$, 13$^{vii}$ to each other. The second position of the locking device is the position shown in for example FIGS. 31 and 32. It can thus be seen that the first section 53 of the second handle part 13$^{vii}$ corresponds to the second position of the locking device 52 and it has such dimensions (i.e. it is so narrow) that the handle parts 12$^{vii}$, 13$^{vii}$ can be pressed together or moved away from each other when the locking device 52 is in the second position.

Correspondingly, the second section 54 of the second handle part corresponds to the first position of the locking device 52 and, as explained, it has such dimensions that the first and second handle part will be locked to each other when the locking device 52 is placed in its first position and the handle parts 12$^{vii}$, 13$^{vii}$ are pressed against each other. In order to keep the locking device 52 in the first position, the internal walls 60 of the locking device 52 may be slightly converging such that the locking device 52 is pressed against the periphery of the handle parts 12$^{vii}$, 13$^{vii}$ when the locking device 52 is pushed from the second position towards the first position. Alternatively, the handle parts 12$^{vii}$, 13$^{vii}$ (or one of them) could become somewhat wider towards the first end 7$^{vii}$ of the handle. Of course, it may also be so that both the handle parts 12$^{vii}$, 13$^{vii}$ and the inner walls 60 of the locking device have a geometry that contributes to squeeze these parts against each other when the locking device is pushed from the second position towards the first position.

Figure 33:
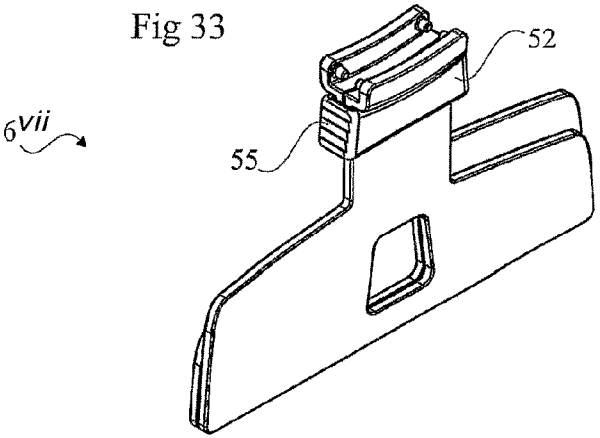
FIG. 33 is a perspective view of the handle and locking device shown in FIG. 32.
Figure 35:
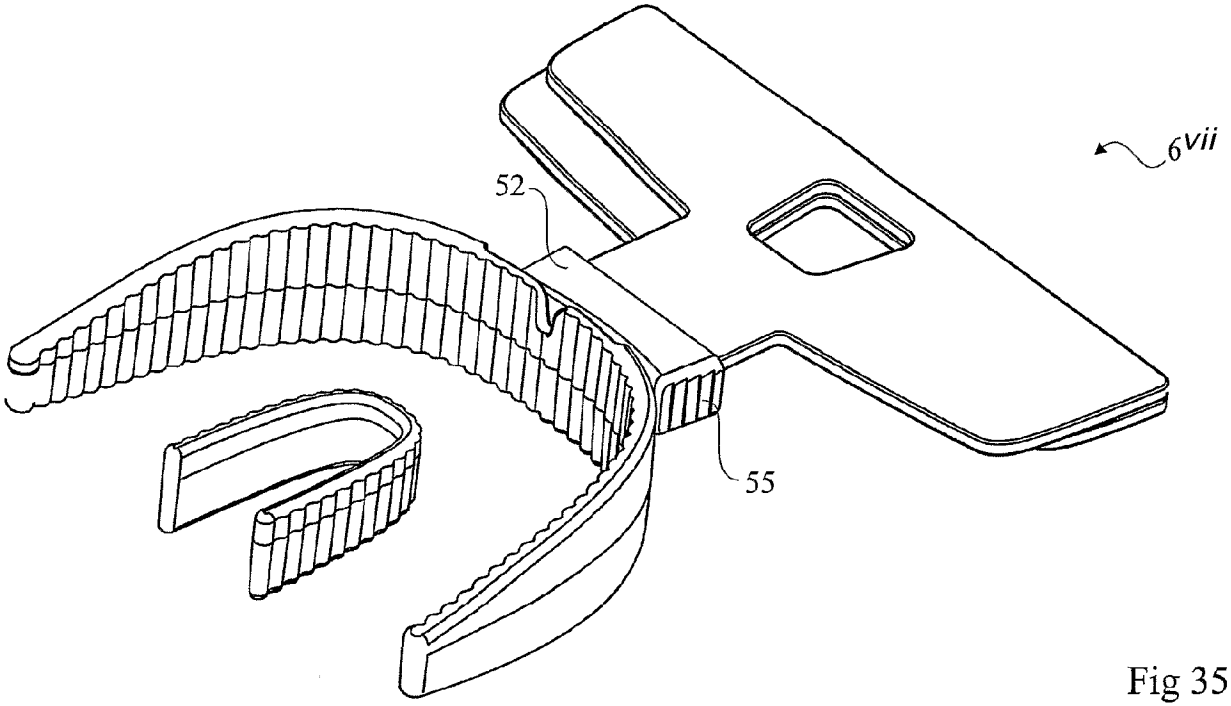
FIG. 35 is a perspective view of a handle connected to a dental impression tray, according to an embodiment.

To connect the handle 6$^{vii}$ to the tray portion 4, the handle 6$^{vii}$ may initially be held in an open position as shown in FIG. 22. The locking device 52 is placed in the second position as indicated in FIGS. 22 and 23. The fastening elements 16$^{vii}$, 17$^{vii}$ of the handle parts 12$^{vii}$, 13$^{vii}$ are connected to the fasteners 18 on the tray section 4 while the handle parts 12$^{vii}$, 13$^{vii}$ are pressed against each other. The locking device 52 is then pushed to the first position of the locking device as shown in FIG. 33. The locking device 52 will now hold the handle parts 12$^{vii}$, 13$^{vii}$ together and the handle will hold the tray portion 4 as indicated in FIG. 35. It should be understood that the fastening elements 16$^{vii}$, 17$^{vii}$ on the handle parts 12$^{vii}$, 13$^{vii}$ may be projections and that the fasteners 18 on the tray section may be recesses into which the fastening elements 16$^{vii}$, 17$^{vii}$ of the handle parts 12$^{vii}$, 13$^{vii}$ are pressed. However, it could also be so that the fastening elements 16$^{vii}$, 17$^{vii}$ on the handle parts 12$^{vii}$, 13$^{vii}$ are parts shaped to define recesses and the fasteners 18 on the tray section could be projections.

While the various embodiments have been described above mainly with reference to a dental impression tray 1, it should be understood that all that has been described above could also be described in terms of methods in connection with the making of dental impressions.

The dental impression tray itself can be made of many different materials. Plastic materials may be suitable, but other materials could also be used, for example ceramic or metallic materials.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The invention claimed is:

1. A kit for making a dental impression and holding the impression for a scanning operation, the kit comprising:

a dental impression tray comprising a tray portion comprising a U-shaped impression section adapted to be loaded with impression material, the tray portion being contoured to fit over at least a part of both an upper dental structure and a lower dental structure to simultaneously obtain an impression of the part of the upper dental structure and the part of the lower dental structure, the tray portion comprising a holding section projecting from a curved surface of the U-shaped impression section, the holding section comprising a first side facing in a first direction and a second side opposite the first side and facing in a second direction that is opposite to the first direction, each of the first side of the holding section and the second side of the holding section comprising a plurality of fasteners, wherein each of the plurality of fasteners is in the form of a hole or a recess;

a holder comprising an alignment part configured to secure the dental impression tray stationary during scanning of the impression of the part of the upper dental structure in a vertical and lateral configuration and during scanning of the impression of the part of the lower dental structure in the same vertical and lateral configuration when the dental impression tray is turned 180°, the holder comprising a plurality of projections or pegs having a shape that is complementary in shape to the fasteners of the first side of the holding section and the fasteners of the second side of the holding section, wherein the fasteners of the first side of the holding section and the fasteners of the second side of the holding section are configured to lock the holding section to the alignment part of the holder, the fasteners of the first side of the holding section and the fasteners of the second side of the holding section each having a form lockable to the holder; and a handle securable to the tray portion and removable from the tray portion, the handle comprising a plurality of fastening elements, wherein each of the plurality of fastening elements is in the form of a projection or a peg, the plurality of fastening elements being complementary in shape to the fasteners of the first side of the holding section and the fasteners of the second side of the holding section, the handle manipulable by a user to align the tray portion in a patient's mouth with [eyes] *at least one facial feature* of the patient, wherein the holder is designed to cooperate with the same fasteners of the holding section of the dental impression tray as the handle, and wherein the handle has a different shape than the holder.

2. The kit of claim 1, wherein the handle comprises a first handle part and a second handle part and wherein the first handle part and the second handle part have a same shape.

3. The kit of claim 2, wherein, when the first handle part is coupled to the second handle part, the first handle part includes a first section overlapping the second handle part and a second section not overlapping the first handle part.

4. The kit of claim 1, wherein the handle comprises a first handle part and a second handle part and wherein the first handle part comprises a first snap fit element and wherein the second handle part comprises a second snap fit element configured to fit with the first snap fit element.

*5. The kit of claim 1, wherein the at least one facial feature comprises eyes of the patient.*

*6. The kit of claim 1, wherein the at least one facial feature comprises an eye and nose of the patient.*

*7. The kit of claim 1, wherein the tray portion comprises at least one fiduciary marker configured to be detected during the scanning of the impression.*

* * * * *